US008129135B2

(12) United States Patent
Ankersmit

(10) Patent No.: US 8,129,135 B2
(45) Date of Patent: Mar. 6, 2012

(54) METHOD FOR DIAGNOSING CARDIOVASCULAR DISEASES

(75) Inventor: Jan Hendrik Ankersmit, Vienna (AT)

(73) Assignee: Medizinische Universität Wien, Vienna (AT)

( * ) Notice: Subject to any disclaimer, the term of this patent is extended or adjusted under 35 U.S.C. 154(b) by 522 days.

(21) Appl. No.: 12/298,209

(22) PCT Filed: Apr. 16, 2007

(86) PCT No.: PCT/AT2007/000173
§ 371 (c)(1),
(2), (4) Date: Oct. 23, 2008

(87) PCT Pub. No.: WO2007/121495
PCT Pub. Date: Nov. 1, 2007

(65) Prior Publication Data
US 2009/0098104 A1 Apr. 16, 2009

(30) Foreign Application Priority Data
Apr. 24, 2006 (AT) .................................. A 694/2006

(51) Int. Cl.
C12Q 1/31 (2006.01)
(52) U.S. Cl. ............................................ 435/23; 435/13
(58) Field of Classification Search ........................ 435/4
See application file for complete search history.

(56) References Cited

U.S. PATENT DOCUMENTS
2010/0028921 A1* 2/2010 Bergmann et al. ............. 435/15

FOREIGN PATENT DOCUMENTS
WO    WO 99/16789    4/1999

OTHER PUBLICATIONS

Nikkari S. et al. Antibodies to Cytoskeletal Proteins in Sera of Patients With Angiographically Assessed Coronary Artery Disease. Atherosclerosis 98(1)Jan. 11-16, 1993.*
Schonbeck U. et al. Ligation of CD40 Activates Interleukin 1 Beta converting Enzyme (Caspase-1) . . . J of Biological Chemistry 272(31)19569-74, Aug. 1997.*
Mattey D. et al. Increased Levels of Antibodies to Cytokeratin 18 in Patients with Rheumatoid Arthritis and Ischaemic Heart Disease. Annals of the Rheumatic Diseases 63(4)420-425, 2004.*
Moon M. et al. Injury Induced Expression of Cytokeratins 8 and 18 . . . Canadian J Physiology Pharmacology 86(5)223-231, May 2008.*
Blankenberg S. et al. Caspase-1 Levels and Casp1 Polymorphisms are Associated with Myocardial Infarction . . . Circulation 112(17), Sup S, pp. U850, Oct. 25, 2005, abstract only.*
Adlbrecht et al., "Elevated levels of interleukin-1beta-converting enzyme and caspase-cleaved cytokeratin-18 in acute myocardial infarction," *European Journal of Clinical Investigation*, 37 (5): 372-380, 2007.
Ankersmit et al., "Increased serum concentrations of soluble CD95/Fas and caspase 1/ICE in patients with acute angina," *Heart*, 90 (2): 151-154, 2004.
Aukrust et al., "Enhanced levels of soluble and membrane-bound CD40 ligand in patients with unstable angina. Possible reflection of T lymphocyte and platelet involvement in the pathogenesis of acute coronary syndromes," *Circulation*, 100 (6): 614-620, 1999.
Austrian International Search Report, issued in Int. App. No. 4B R 219/2006, mail date May 22, 2006.
Balbay et al., "Circulating interleukin-1 beta, interleukin-6, tumor necrosis factor-alpha, and soluble ICAM-1 in patients with chronic stable angina and myocardial infarction," *Angiology*, 52 (2): 109-114, 2001.
Bancher-Todesca et al., "Placental expression of cytokeratin 18 and serum levels of tissue polypeptide antigen in women with pregnancy-induced hypertension," *Hypertension in Pregnancy: Official Journal of the International Society for the Study of Hypertension in Pregnancy*, 20 (1): 89-98, 2001.
Bombeli et al., "Apoptotic vascular endothelial cells become procoagulant," *Blood*, 89 (7): 2429-2442, 1997.
Braunwald, "Unstable angina. A classification," *Circulation*, 80 (2): 410-414, 1989.
Caulín et al., "Caspase cleavage of kareatin 18 and reorganization of intermediate filaments during epithelial cell apoptosis," *J. Cell. Biol.*, 138 (6): 1379-1394, 1997.
Fauvel et al., "Differential effects of caspase inhibitors on endotoxin-induced myocardial dysfunction and heart apoptosis," *Am. J. Physiol. Heart Circ. Physiol.*, 280 (4): H1608-1614, 2001.
Fernandes-Alnemri et al., "In vitro activation of CPP32 and Mch3 by Mch4, a novel human apoptotic cysteine protease containing two FADD-like domains," *PNAS USA*, 93 (15): 7464-7469, 1996.
Frantz et al., "Targeted deletion of caspase-1 reduces early mortality and left ventricular dilatation following myocardial infarction," *J. Mol. Cell. Cardiol.*, 35 (6): 685-694, 2003.
International Search Report and Written Opinion, issued in Int. App. No. PCT/AT2007/000173, mail date Jan. 17, 2008.
Kadyrov et al., "Expression of a cytokeratin 18 neo-epitope is a specific marker for trophoblast apoptosis in human placenta," *Placenta*, 22 (1): 44-48, 2001.
Kostura et al., "Identification of a monocyte specific pre-interleukin 1 beta convertase activity," *PNAS USA*, 86 (14): 5227-5231, 1989.
Kramer et al., "Differentiation between cell death modes using measurements of different soluble forms of extracellular cytokeratin 18," *Cancer Res.*, 64 (5): 1751-1756, 2004.

(Continued)

Primary Examiner — Ralph Gitomer
(74) Attorney, Agent, or Firm — Fulbright & Jaworski LLP

(57) ABSTRACT

Method for diagnosing a cardiovascular disease in an individual comprising the steps of: providing a sample of an individual; determining the amount of cytokeratin-18 (CK-18) or fragments thereof and/or interleukin-1β precursor (IL-1β precursor) in the sample; comparing the amount of CK-18 or fragments thereof and/or IL-1β precursor in the sample to the amount of CK-18 or fragments thereof and/or IL-1β precursor present in a reference control of at least one individual not suffering from a cardiovascular disease; and diagnosing a cardiovascular disease if the amount of CK-18 or fragments thereof in the sample is increased in comparison to the amount of CK-18 or fragments thereof in the reference control and/or the amount of IL-1β precursor in the sample is decreased in comparison to the amount of IL-1β precursor in the reference control.

17 Claims, 2 Drawing Sheets

OTHER PUBLICATIONS

Ku et al., "Apoptosis generates stable fragments of human type I keratins," *J. Biol. Chem.*, 272 (52): 33197-33203, 1997.

Kubota et al., "Overexpression of tumor necrosis factor—alpha activates both anti- and pro-apoptotic pathways in the myocardium," *J. Mol. Cell. Cardiol.*, 33 (7): 1331-1344, 2001.

Leers et al., "Immunocytochemical detection and mapping of a cytokeratin 18 neo-epitope exposed during early apoptosis," *J. Pathol.*, 187 (5): 567-572, 1999.

Mach et al., "Functional CD40 ligand is expressed on human vascular endothelial cells, smooth muscle cells, and macrophages: implications for CD40-CD40 ligand signaling in atherosclerosis," *PNAS USA*, 94 (5): 1931-1936, 1997.

Mattey et al., "Increased levels of antibodies to cytokeratin 18 in patients with rheumatoid arthritis and ischaemic heart disease," *Ann. Rheum. Dis.*, 63(4): 420-425, 2004.

Mutin et al., "Direct evidence of endothelial injury in acute myocardial infarction and unstable angina by demonstration of circulating endothelial cells," *Blood*, 93 (9): 2951-2958, 1999.

Nicholson et al., "Identification and inhibition of the ICE/CED-3 protease necessary for mammalian apoptosis," *Nature*, 376 (6535): 37-43, 1995.

Nikkari et al., "Antibodies to cytoskeletal proteins in sera of patients with angiography assessed coronary artery disease," *Atherosclerosis*, 98 (1): 11-16, 1993.

Ohashi et al., "Soluble CD40 ligand and interleukin-6 in the coronary circulation after acute myocardial infarction," *Int. J. Cardiol.*, 2005.

Rentrop, "Thrombi in acute coronary syndromes: revisited and revised," *Circulation*, 101 (13): 1619-1626, 2000.

Rossi et al., "Different quantitative apoptotic traits in coronary atherosclerotic plaques from patients with stable angina pectoric and acute coronary syndromes," *Circulation*, 110 (13): 1767-1773, 2004.

Schaafsma and Ramaekers, "Cytokeratin subtyping in normal and neoplastic epithelium: basic principles and diagnostic applications," *Pathol. Annu.*, 29 (pt. 1): 21-62, 1994.

Schmidt and Abdulla, "Down-regulation of IL-1 beta biosynthesis by inducers of the heat-shock response," *J. Immunology*, 141 (6): 2027-2034, 1988.

Schutte et al., "Keratin 8/18 breakdown and reorganization during apoptosis," *Exp. Cell. Res.*, 297 (1): 11-26, 2004.

Simon et al., "Circulating levels of IL-1 beta, a prothrombotic cytokine, are elevated in unstable angina versus stable angina," *J. Thromb. Thrombolysis*, 9 (3): 217-222, 2000.

Syed et al., "Proapoptotic effects of caspase-1/interleukin-converting enzyme dominate in myocardial ischemia," *Circ. Res.*, 96 (10): 1103-1109, 2005.

Tewari et al., "Yama/CPP32 beta, a mammalian homolog of CED-3, is a CrmA-inhibitable protease that cleaves the death substrate poly(ADP-ribose) polymerase," *Cell*, 81 (5): 801-809, 1995.

Thornberry et al., "A novel heterodimeric cysteine protease is required for interleukin-1 beta processing in monocytes," *Nature*, 356 (6372): 768-774, 1992.

Thornberry, "Interleukin-1 beta converting enzyme," *Meth. Enzymol.*, 244: 615-631, 1994.

Tokac et al., "The role of inflammation markers in triggering acute coronary events," *Heart Vessels*, 18 (4): 171-176, 2003.

Topol, "Toward a new frontier in myocardial reperfusion therapy: emerging platelet preeminence," *Circulation*, 97 (2): 211-218, 1998.

Valgimigli et al., "Endothelial dysfunction in acute and chronic coronary syndromes: evidence for a pathogenetic role of oxidative stress," *Arch. Biochem. Biophys.*, 420 (2): 255-261, 2003.

Valgimigli et al., "Serum from patients with acute coronary syndromes displas a proapoptotic effect on human endothelial cells: a possible link to pan-coronary syndromes," *Circulation*, 107 (2): 264-270, 2003.

Wang et al., "Clinical significance of serum cytokines IL-1beta, sIL-2R, IL-6, TNF-alpha, and IFN-v in acute coronary syndrome," *Chin. Med. Sci. J.*, 19 (2): 120-124, 2004.

Willerson, "Sytemic and local inflammation in patients with unstable atherosclerotic plaques," *Prog. Cardiovasc. Dis.*, 44 (6): 469-478, 2002.

Yaoita et al., "Attenuation of ischemia/reperfusion injury in rats by a caspase inhibitor," *Circulation*, 97 (3): 276-281, 1998.

Zal et al., "Heat-shock protein 60-reactive CD4+CD28null T cells in patients with acute coronary syndromes," *Circulation*, 109 (10): 1230-1235, 2004.

* cited by examiner

METHOD FOR DIAGNOSING CARDIOVASCULAR DISEASES

The present invention relates to a method for diagnosing a cardiovascular disease.

According to the World Health Organization (WHO; Geneva) cardiovascular diseases are the cause of more than 15 million deaths in the world each year. They account for 50% of all deaths in several developed countries, and more than 50% in Africa and Western and Southeast Asia. They are also the major cause of death in adults. In addition, many cardiovascular incidents are not necessarily fatal, but may impair the ability to live a normal daily life, resulting in enormous healthcare costs to society.

Due to improved acute and chronic-medications and surgical procedures, as well as lifestyle and diet changes, there have been significant declines in total cardiovascular disease mortality over the past few decades. Still, because of these high incidences and mortality rates, cardiovascular diseases are the subject of enormous investment by both the biotechnology and pharmaceutical industries.

However, an efficient treatment and prevention of cardiovascular diseases does not only involve the administration of appropriate medicaments but requires also reliable diagnostic tools. Therefore the identification and use of molecular markers of cardiovascular diseases for early diagnosis and prevention is of major importance. For example, cardiac troponins are selectively released by damaged myocardiocytes. The specificity of this event is high enough for improvements in the diagnosis of acute cardiac ischemic disorders. Further it enables the clinician to predict the risk and outcome scenarios for patients more reliably.

Further, the search for biological markers indicative for atherosclerosis formation, its progression and destabilization is of enormous relevance in the clinical setting of acute coronary syndromes and other clinical entities related to ischaemic events, e.g. stroke.

Today, multiple lines of evidence suggest that atherosclerosis is a chronic inflammatory disease and implicates components of the immune system in atherogenesis. Recently, research work identified the participation of potent immune mediator CD40 and its counterpart CD40 ligand (CD40L or CD154) to be involved in inflammation. Previously, markers of general inflammation such as high-sensitivity C-reactive protein (hsCRP) and interleukin-6, as well as serum amyloid were suggested to be related with adverse outcomes in patients with coronary heart disease.

It is an object of the present invention to provide means and methods for diagnosing cardiovascular diseases in an individual. A further object is a method for discriminating stable from unstable angina pectoris. Another further object of the present invention is to provide means for the treatment of cardiovascular diseases, in particular diseases associated with thrombosis.

Therefore, the present invention relates to a method for diagnosing a cardiovascular disease in an individual comprising the steps of:
  providing a sample of an individual,
  determining the amount of cytokeratin-18 or fragments thereof (CK-18) and/or interleukin-1β precursor (IL-1β precursor) in said sample,
  comparing the amount of CK-18 or fragments thereof and/or IL-1β precursor in said sample to the amount of CK-18 or fragments thereof and/or IL-1β precursor present in a reference control of at least one individual not suffering from a cardiovascular disease and
  diagnosing a cardiovascular disease if the amount of CK-18 or fragments thereof in the sample is increased in comparison to the amount of CK-18 or fragments thereof in the reference control and/or the amount of IL-1β precursor in the sample is decreased in comparison to the amount of IL-1β precursor in the reference control.

Further, it was found that the amount of CK-18 or fragments thereof and IL-1β precursor in a sample of an individual suffering or suspected of suffering from a cardiovascular disease compared to a sample of a healthy individual indicates a cardiovascular disease. The amount of CK-18 or fragments thereof and IL-1β precursor in a sample of an individual suffering from a cardiovascular disease is increased and decreased, respectively, in comparison to the amount of said markers in a sample obtained from a healthy individual not suffering from a cardiovascular disease.

Local and systemic inflammation play a major role in cardiovascular diseases, in particular in acute coronary syndromes (ACS), including unstable angina (UA) and acute myocardial infarction (AMI). Various data indicate that apoptosis is a key event during the development and progression of the atherosclerotic plaque. Although AMI has been clearly demonstrated to occur as a direct result of ischemia-induced myocyte necrosis, apoptosis has been described as an important contributing entity after occlusion of the coronary artery. Mechanistically, thrombus formation after plaque rupture accounts for vessel occlusion in AMI and contributes to compromised flow in UA. Urgent percutaneous coronary intervention (PCI) is the state-of the art option for the treatment of patients with ACS, and is associated with higher reperfusion rates and better outcome than thrombolytic therapy. Nevertheless, PCI carries the risk of mobilizing thrombotic and thrombogenic material, causing distal embolization and microcirculatory impairment, which may limit myocardial salvage.

Several thrombectomy devices were introduced in the clinical arena to allow fragmentation and removal of intracoronary thrombotic material in the setting of AMI. In prospective, randomized trials for example the X-sizer thrombectomy device has been shown to improve epicardial flow and ST-segment resolution. However, no improvement of survival or increased myocardial salvage could be demonstrated in these studies. Although the effect of acute thrombectomy on survival, ventricular function and improvement of quality of life were not proven in large multicenter trials until today, the technique offers the possibility to harvest blood samples from the site of acute arterial thrombosis in the coronary artery to allow to investigate proteins known to be associated with inflammation and apoptosis.

Apoptosis refers to the morphological alterations exhibited by "actively" dying cells that include cell shrinkage, membrane blebbing, chromatin condensation, and DNA fragmentation. Apoptotic cell death can result either from developmentally controlled activation of endogenous execution programs or from transduction of death signals triggered by a wide variety of exogenous stimuli. A major pathway requires triggering of the receptor for interleukin-1β-converting enzyme (ICE), a cysteine protease protein-32-like family, homologous to the gene product of the *Caenorhabditis elegans* cell death gene ced-3. Other proteins known to be associated with inflammation and apoptosis include IL-1β and IL-1β precursor (IL-1βp), TNF-α and TNF-R1/CD120a, CD95 and CD95L/CD178, CD40 and CD40L/CD154. Moreover, patients with UA show increased concentrations of soluble shed membrane components, originating from activated CD3+ cells, macrophages and endothelial cells, indicating increased intravascular peripheral apoptotic turnover. These shed membrane particles were reported to have increased procoagulative ability. Further, it was found that patients with ischemic heart disease develop antibodies against cytokeratin 18 (CK-18) or fragments thereof, a cytoskeleton product being present in endothelial cells and cardiac microvasculature undergoing apoptosis.

All of these markers have been described in publications to be positive prognosticators of coronary heart disease and the p values were described to be in the range of 0.04-0.05.

The term "reference control", as used herein, means a sample of preferably the same source (e.g. blood, serum etc.) which is obtained from at least one healthy individual to be compared to the sample of the individual to be analysed. In order to receive comparable results the reference control as well as the sample of the individual should be obtained, handled and treated in the same way. The number of healthy individuals in order to obtain a reference control value may be at least one, preferably at least two, more preferably at least five, most preferably at least ten, in particular at least 20. However, the values may also be obtained from at least 100, 1000 or 10000 individuals.

"Amount" and its synonymously used term "level" as used in the context of the present invention means the concentration of a marker present in a sample.

The terms "the amount is increased in comparison to" and "the amount is decreased in comparison to", as used herein, means the amount determined in the sample to be analysed diverges with statistical significance from the control or "normal" (=healthy) value, e.g. at least 30%, preferably at least 50%, more preferably at least 100%, most preferably at least 200%, from the amount of the reference control. As used herein, the term "CK-18 or fragments thereof" refers to CK-18 and the specific fragments thereof which are e.g. obtained by caspase mediated cleavage of cytokeratin-18 in apoptotic cells and which are released from said cells (see e.g. Kramer G et al. Cancer Res. (2004) 64:1751-1756). Specific fragments are those which are specifically recognisable as CK-18 degradation products produced by physiological or pathological processes inside the human body. Specific fragments of CK-18 may also be produced in vitro e.g. by protease or chemical treatment of CK-18 or (by further fragmentation of) physiologically/pathologically generated fragments. Such CK-18 fragments must—in any case—be CK-18 specific (i.e. to be unambiguously identifiable as CK-18 fragments) and should be at least 8 amino acid residues long, preferably at least 10 amino acids long, especially at least 15 amino acids long. These fragments should have (or be selected to have) a characteristic (unique) amino acid sequence to be specifically recognised. Preferred CK-18 fragments have a length of 50 to 400 amino acid residues, preferably of 100 to 350 amino acid residues, especially of 150 to 300 amino acid residues. CK-18 or fragments thereof may be detected by specific polyclonal or monoclonal antibodies (which do not recognise or cross-react with other proteins, such as other cytokreatins). A significant number of such anti-CK-18 antibodies specifically recognising CK-18 or fragments thereof are commercially available. An example for such an antibody is antibody MB30 recognising the sequence EDFNLGDALD in a caspase-cleaved CK-18 fragment having a cleavage site after DALD (EP 1 019 438 A). This antibody is even specific for this fragment and does not recognise the uncleaved CK-18. Accordingly, detection means (e.g. antibodies) which are not only CK-18 specific, but specific for a certain CK-18 fragment are preferred means for detecting CK-18 fragments according to the present invention. Caspase-cleaved fragments of CK-18 are specifically preferred CK-18 fragments according to the present invention.

According to the present invention an "individual not suffering from a cardiovascular disease" means an individual whose CK-18 (or fragments thereof), IL-1β precursor and/or caspase-1 (ICE) levels resemble those of a healthy individual.

According to a preferred embodiment of the present invention the cardiovascular disease is atherosclerosis, a coronary heart disease, an acute coronary symptom, preferably unstable angina pectoris or acute myocardial infarction, stable angina pectoris, stroke, preferably ischemic stroke, inflammation or autoimmune disease associated artheriosclerosis or restenosis.

The term "cardiovascular disease" as used herein refers to any disease or disorder affecting the vascular system, including the heart and blood vessels. A vascular disease or disorder includes any disease or disorder characterised by vascular dysfunction, including, for example, intravascular stenosis (narrowing) or occlusion (blockage), due to the development of atherosclerotic plaque and diseases and disorders resulting therefrom. Particularly preferred cardiovascular diseases are selected from the group consisting of atherosclerosis, a coronary heart disease, an acute coronary symptom, preferably unstable angina pectoris or acute myocardial infarction, stable angina pectoris, stroke, preferably ischemic stroke, inflammation or autoimmune disease associated artheriosclerosis or restenosis.

According to another preferred embodiment of the present invention the amount of caspase-1 (ICE) in the sample is additionally determined, compared with the amount of ICE present in the reference control and diagnosed to a cardiovascular disease if the amount of ICE in the sample is increased in comparison to the amount of ICE in the reference control.

The determination of the amount of ICE in a sample in combination with the determination of the amounts of CK-18 or fragments thereof and/or IL-1β precursor allows an even more accurate diagnosis.

Another aspect of the present invention relates to a method for discriminating between stable and unstable angina pectoris or for diagnosing stable and unstable angina pectoris or for risk evaluation of restenosis after percutaneous coronary intervention in an individual comprising the steps of:

providing a sample of an individual, determining the amount of cytokeratin-18 or fragments thereof (CK-18 or fragments thereof) and/or interleukin-1β precursor (IL-1β precursor) in said sample, comparing the amount of CK-18 or fragments thereof and/or IL-1β precursor in said sample to the amount of CK-18 or fragments thereof and/or IL-1β precursor present in at least one reference control of at least one individual suffering from stable or unstable angina pectoris, diagnosing stable angina pectoris if the amount of CK-18 or fragments thereof in the sample is decreased and the amount of IL-1β precursor in the sample is increased in comparison to amount of CK-18 or fragments thereof and/or IL-1β precursor in the reference control of at least one individual suffering from unstable angina pectoris (it is also possible to diagnose stable angina pectoris when the determined marker amounts are compared to the levels in an individual suffering from stable angina pectoris).

Angina pectoris is the result of myocardial ischemia, which is caused by an imbalance of myocardial oxygen supply and demand. Specifically, demand exceeds supply due to inadequate blood supply. The heart accounts for a small percentage of total body weight, but is responsible for 7% of body oxygen consumption. Cardiac tissue metabolism is highly aerobic and has very little reserve to compensate for inadequate blood supply. When the blood supply is reduced to levels that are inadequate for myocardial demand, the tissue rapidly becomes hypoxic and toxic cellular metabolites cannot be removed. Myocardial cells rapidly use oxygen supplies remaining in the local microvasculature, and the time span that aerobic metabolism continues is indirectly proportional to the degree of arterial occlusion. Once the oxygen supply has been exhausted, oxidative phosphorylation cannot continue because oxygen is no longer available as an electron acceptor, pyruvate cannot be converted to acetyl coenzyme A and enter the citric acid cycle. Myocardial metabolism switches to anaerobic metabolism using glycogen and glucose stores, and pyruvate is fermented to lactate. Lactate accumulation is the primary cause of chest pain in individuals with ACS. As ischemia continues, cardiac tissue becomes more acidic than lactate and other acidic intermediates accumulate, ATP levels decrease, and available energy sources are depleted. Cardiac tissue can recover if it is reperfused 15-20 minutes after an ischemic event. After the cellular glycogen stores have been depleted, the cell gradually displays features of necrosis, including mitochondrial swelling and loss of cell membrane integrity. Upon reperfusion, these damaged cells die, possibly as a result of the cell's inability to maintain ionic equilibrium. A loss of membrane integrity causes the cell's cytosolic contents to be released into the circulation.

Stable angina, unstable angina, and myocardial infarction share one common feature: constricting chest pain associated with myocardial ischemia. Angina is classified as stable or unstable through a physician's interpretation of clinical symptoms, with or without diagnostic ECG changes. The classification of angina as "stable" or "unstable" does not refer to the stability of the plaque itself, but rather, the degree of exertion that is required to elicit chest pain. Most notably, the classification of chest pains as stable or unstable angina (or even mild myocardial infarction) in cases other than definitive myocardial infarction is completely subjective. The diagnosis, and in this case the distinction, is not made by angiography, which may quantify the degree of arterial occlusion, but rather by a physician's interpretation of clinical symptoms.

Stable angina is characterised by constricting chest pain that occurs upon exertion or stress, and is relieved by rest or sublingual nitro-glycerine. Coronary angiography of patients with stable angina usually reveals 50-70% obstruction of at least one coronary artery. Stable angina is usually diagnosed by the evaluation of clinical symptoms and ECG changes. Patients with stable angina may have transient ST segment abnormalities, but the sensitivity and specificity of these changes associated with stable angina are low.

Unstable angina is characterised by constricting chest pain at rest that is relieved by sublingual nitro-glycerine. Anginal chest pain is usually relieved by sublingual nitro-glycerine, and the pain usually subsides within 30 minutes. Unstable angina represents the clinical state between stable angina and AMI and is thought to be primarily due to the progression in the severity and extent of atherosclerosis, coronary artery spasm or haemorrhage into non-occluding plaques with subsequent thrombotic occlusion. Coronary angiography of patients with unstable angina usually reveals 90% or greater obstruction of at least one coronary artery, resulting in an inability of oxygen supply to meet even baseline myocardial oxygen demand. Slow growth of stable atherosclerotic plaques or rupture of unstable atherosclerotic plaques with subsequent thrombus formation can cause unstable angina. Both of these causes result in critical narrowing of the coronary artery. Unstable angina is usually associated with atherosclerotic plaque rupture, platelet activation, and thrombus formation. Unstable angina is usually diagnosed by clinical symptoms, ECG changes, and changes in cardiac markers. Treatments for patients with unstable angina include nitrates, aspirin, GPIIb/IIIa inhibitors, heparin, and beta-blockers. Patients may also receive angioplasty and stents. Finally, patients with unstable angina are at risk for developing acute myocardial infarction.

Therefore, in order to provide a reliable differential diagnosis between stable and unstable angina pectoris and optionally also between stable angina pectoris, unstable angina pectoris and acute myocardial infarction levels of CK-18 or fragments thereof and/or IL-1β precursor and optionally ICE in a sample obtained from an individual suspected to suffer from one of said conditions are determined and compared to their respective levels in individuals suffering from one of those conditions.

Levels of CK-18 or fragments thereof and ICE in individuals suffering from stable angina pectoris are decreased when compared to levels found in individuals suffering from unstable angina pectoris and acute myocardial infarction.

In contrast thereto, levels of IL-1β precursor are increased in individuals suffering from stable angina pectoris when compared to those levels found in individuals suffering from unstable angina pectoris.

Since this method allows to clearly distinct between stable and unstable angina pectoris in an individual, the data obtained may be useful for designing an optimal and appropriate treatment of an individual suffering either from stable or unstable angina pectoris and acute myocardial infarction.

According to a preferred embodiment of the present invention relating to the method for discriminating between stable and unstable angina pectoris or for diagnosing stable and unstable angina pectoris in an individual the amount of caspase-1 (ICE) in the sample is further determined, compared with the amount of ICE present in the reference control and diagnosed stable angina pectoris if the amount of ICE in the sample is decreased in comparison to the amount of ICE in the reference control of at least one individual suffering from unstable angina pectoris.

In addition, the method according to the present invention relating to the method for discriminating between stable and unstable angina pectoris or for diagnosing stable and unstable angina pectoris in an individual may involve the determination of the amount of CK-18 or fragments thereof and/or IL-1β precursor and of ICE. It is also possible to combine the quantification of the single markers: CK-18 or fragments thereof and IL-1β precursor; CK-18 or fragments thereof, IL-1β precursor and ICE; CK-18 or fragments thereof and ICE; IL-1β precursor and ICE.

According to a preferred embodiment of the present invention the amount of cytokeratin-18 or fragments thereof, caspase-1 (ICE) and interleukin-1β precursor (IL-1 precursor) is immuno-logically determined, preferably by enzyme linked immunosorbent assay, by radio immuno assay or by Western blot analysis.

Protein levels of CK-18 or fragments thereof, ICE and IL-1β precursor in the sample can be assayed using any suitable method known in the art. For example, the enzyme ICE can be quantified by an assay based upon its catalytic activity (e.g. Thornberry, N. A. et al. (1992) Nature 356, 768-74; Nicholson, D. W. et al. (1995) Nature 376, 37-43; Tewari, M. et al. (1995) Cell 81, 801-9; Fernandes-Alnemri, T. et al. (1996) PNAS USA 93, 7464-9; Thornberry, N. A. (1994) Meth. Enzymol. 244, 615-31) or based upon the quantification of protein amount contained in a sample. For determining the amount of CK-18 or fragments thereof, e.g., several immunological assays are known in the art (e.g. Kramer G. et al., Cancer Res. (2004) 64:1751-1756). For example anti-body-based techniques may preferably be employed for all markers in a method according to the present invention. For example, specific recognition is provided by a primary antibody (poly-clonal or monoclonal) and a secondary detection system is used to detect presence (or binding) of the primary antibody. Detectable labels can be conjugated to the secondary antibody, such as a fluorescent label, a radiolabel or an enzyme (e.g., alkaline phosphatase, horseradish peroxidase) which produces a quantifiable, e.g. colored, product. In another suitable method, the primary antibody itself can be detectably labelled. As a result, immunohistological labelling of a tissue section is provided. In one embodiment, an extract is produced from a biological sample (e.g. blood, tissue, cells) for analysis. Such an extract (e.g. a detergent extract) can be subjected to western-blot or dot/slot assay for the level of the protein of interest, using routine immunoblotting methods (Jalkanen et al., J. Cell. Biol., 101:976-985 (1985); Jalkanen et al., J. Cell. Biol., 105:3087-3096 (1987)).

Other useful antibody-based methods include immunoassays, such as the enzyme-linked immunosorbent assay (ELISA) and the radioimmunoassay (RIA). For example, a protein-specific monoclonal antibody can be used both as an immunoadsorbent and as an enzyme-labelled probe to detect and quantify protein of interest. The amount of such protein present in a sample can be calculated by reference to the amount present in a standard preparation using a linear regression computer algorithm (see Iacobilli et al., Breast Cancer Research and Treatment, 11:19-30 (1988)). In another embodiment, two different monoclonal anti-bodies to the protein of interest can be employed, one as the immunoadsorbent and the other as an enzyme-labelled probe.

The sample to be analysed is preferably a body fluid, preferably blood, more preferably plasma or serum.

All marker polypeptides according to the present invention may be detected and quantified in (whole) blood as well as in plasma or serum, preferably in soluble or solubilised form.

According to a preferred embodiment of the present invention the sample is obtained from the femoral artery. Control plasma samples are obtained from stable and instable angina pectoris patients from the cubita (both sampling methods represent peripheral blood flow).

Another aspect of the present invention relates to a kit for diagnosing a cardiovascular disease, for discriminating between stable and unstable angina pectoris or for diagnosing stable and unstable angina pectoris in an individual or for evaluating the risk of an individual to obtain a thrombus in the cardiovascular system comprising:
 means for detecting cytokeratin-18 or fragments thereof (CK-18), caspase-1 (ICE) and/or interleukin-1β precursor (IL-1β precursor) and
 a reference control.

In clinical practice the diagnosis of cardiovascular diseases, discrimination between stable and unstable angina pectoris as well as the diagnosis of angina pectoris is of particular interest since it allows the practitioner to evaluate the risks of the patient of being suseptible for acute myocardial infarction, severe cardiac arrhythmias like ventricular tachycardia and fibrillation or cardiac arrest leading to sudden death. On the basis of the results obtained by the method and kit according to the present invention suitable treatments and/or surgical interventions may be applied. The kit of the present invention may also be employed for evaluating the risk of an individual to obtain a thrombus in the cardiovascular system. An elevated level of CK-18 or fragments thereof compared to a healthy individual indicates a risk to obtain a thrombus. Hence the present invention relates also to a method for evaluating said risk.

According to a preferred embodiment of the present invention said means comprise antibodies directed against CK-18 or fragments thereof, ICE and IL-1β precursor.

Said antibodies may be polyclonal or monoclonal and may be conjugated to an appropriate label which allows the detection of binding of specific antibodies to CK-18 or fragments thereof, ICE and IL-1β precursor. It is also possible to use secondary antibodies directed to antibodies that bind to CK-18 or fragments thereof, ICE and IL-1β. In case the activity of ICE is determined a peptide or polypeptide substrate may further be enlarged (e.g. Thornberry, N. A. et al. (1992) Nature 356, 768-74; Nicholson, D. W. et al. (1995) Nature 376, 37-43; Tewari, M. et al. (1995) Cell 81, 801-9; Thornberry, N. A. (1994) Meth. Enzymol. 244, 615-31)

According to another preferred embodiment of the present invention the reference control is obtained from at least one individual not suffering from a cardiovascular disease or from at least one individual suffering from stable or unstable angina pectoris.

The cardiovascular disease to be detected by the kit according to the present invention may be atherosclerosis, a coronary heart disease, an acute coronary symptom, preferably unstable angina pectoris or acute myocardial infarction, stable angina pectoris, stroke, inflammation or autoimmune disease associated artheriosclerosis or restenosis.

Another aspect of the present invention relates to the use of a compound degrading cytokeratin-18 or fragments thereof for the manufacture of a medicament for the treatment of thrombosis (e.g. coronary thrombosis, deep venous thrombosis, superficial venous thrombosis, thrombosis of the portal vein) and thrombosis related diseases. Surprisingly CK-18 or fragments thereof was found in a thrombus formed in a blood vessel of an individual suffering from a cardiovascular disease. Suitable low-molecular caspase cleaved CK-18 fragments are found in thrombi. Thrombosis and thrombus dependent vascular diseases can occur in all human organs, e.g. Chronic thromboembolic pulmonary hypertension (CTPH) or susceptibility to acquired peripheral veno disease.

Thrombi are abnormal blood clots inside a blood vessel. The consequence of thrombosis is an obstruction of the blood flow. Since the leading cause of death in the Western world is the formation of an abnormal blood clot inside a blood vessel, it is important for healthy people to take steps to prevent thrombosis. For those with risk factors for developing thrombosis, sudden actions must be taken to protect against stroke, heart attack, kidney failure, pulmonary embolus, etc.

Thrombi can be formed in an artery, a vein or in the chambers of the heart. Thrombi are formed in the arteries under high pressure and flow conditions and are composed of platelet aggregates bound together by intrinsic fibrin protein strands. Clots in veins are formed under low flow conditions, are composed predominantly of red cells with few platelets, and contain a large amount of interspersed fibrin strands.

These thrombi may remain static in the vessel, but clots can become mobile or embolize. When a clot travels from a lower extremity vein to the lungs, the consequence is a pulmonary embolism and/or a pulmonary infarction (lung cell death). Similarly, when a clot moves from the heart or the carotid artery to the brain, it can cause a stroke. When a clot travels to a position that occludes, or blocks, the coronary artery, a heart attack (myocardial infarction) can be developed. Certain conditions such as irregular heart rhythms (e.g. atrial fibrillation) and valvular diseases (e.g. mitral stenosis) cause atrial chamber enlargement and inefficient atrial chamber contractions. Therefore the risk of clots to be formed in the atria that can mobilize to the brain and cause a stroke is increased.

The prevention of thrombosis is essential in order to significantly reduce cardiovascular diseases. Cardiovascular disease remains the leading cause of death at approximately 1 million deaths per year. This is about twice the incidence of yearly cancer deaths. Of these cardiovascular deaths, coronary artery disease represents approximately 51%, while strokes represent 16%. These diseases involve thrombosis in their evolution and make up a significant percentage of all cardiovascular deaths. In addition, thrombosis is a common killer of cancer patients. Therefore, it becomes paramount to optimize the prevention and the treatment of thrombosis in order to reduce the high incidence of deaths from cardiovascular as well as other diseases.

The symptoms of thrombosis are dependant on the localization of the clot formed. During a heart attack, which sometimes is due to a clot lodging in a coronary artery, the onset of associated symptoms usually occurs suddenly. When the coronary artery involved is a minor vessel and the vessel is occluded (blocked) by the clot at its terminal end, the heart attack may be without any symptoms at all. However, when the clot is large and suddenly occludes in the left main coronary artery, the entire blood supply to the left ventricle is suddenly cut off and the heart attack is massive and abruptly fatal. Branches of the left or right main coronary arteries can be occluded by embolisms or, more commonly, by small clots that form on the wall of a coronary artery and mix with oxidized LDL and fibrinogen to occlude the vessel, forming what is called an atheroma, and narrowing the lumen of the involved coronary artery.

This occlusion often causes the classic symptoms of a sudden heart attack: angina-related chest pain, shortness of breath, cold and clammy perspiration, cold extremities, overwhelming anxiety, nausea, profound weakness, dizziness, difficulty concentrating, chest fluttering, and palpitations or other irregular heart beats. The classic chest pain felt during a heart attack resembles a heavy, crushing, constricting sensation. This pain can originate in the chest, the left or right arm, the shoulders, or even the jaw. The pain often extends from the chest down the left arm. However, the extension of pain can move from the chest to the right arm or even to the jaw. When associated with an on-going heart attack, the pain tends to last 10-15 minutes rather than 1-3 minutes prior to the heart attack.

In cases where the occlusion is less severe or in cases of impaired nerve supply (e.g., as in diabetic neuropathy), a heart attack can occur without any symptoms and even present to the emergency room with a normal ECG. In this situation, the heart attack is diagnosed by identifying positive cardiac enzymes in the blood. If classic heart attack symptoms manifest, acetylsalicylic acid, for instance, may be administered as a first aid step.

The symptoms associated with a thrombotic stroke are variable, depending on whether the stroke occurs from a sudden embolism or gradual clot formation. In a cerebral embolic stroke, the symptoms are rapid in onset and often peak within a few seconds. Victims may experience seizures and a headache on the affected side due to the sudden onset of symptoms. In a cerebral thrombotic stroke, the onset is over minutes or hours and occasionally the stroke progresses in stages over days or weeks.

The symptoms that occur during a stroke depend upon the region of the brain that is injured. For example, when the region supplying the eyes (the retinal region) is involved, patients experience transient blackouts and the sense that a shade is being pulled over their eyes. When the cerebrum is involved, contralateral monoparesis, hemiparesis, localized tingling, numbness, hemianopic visual loss, aphasia and losses of consciousness can occur. When the vertebrobasilar region is involved, patients experience bilateral visual disturbances (dim, gray, blurred vision, or temporary total blindness called diplopia). Vertebrobasilar episodes cause symptoms to be induced by abrupt position changes while carotid episodes do not. When the labyrinth or medulla is involved, vertigo, unsteadiness, nausea, and vomiting occur. When the brainstem is involved, patients experience slurred speech, dysarthria, dysphasia, numbness, weakness, and all four-limb paresthesia. "Drop" attacks from sudden loss of postural tone are symptoms of a stroke that is basilar in origin.

The symptoms associated with the onset of a pulmonary embolism or infarction can be non-specific and often vary in frequency and intensity. This depends upon the extent of pulmonary vascular occlusion, the functional strength of the heart before the embolism occurred, and the size of the emboli. Small emboli, or microemboli, may be asymptomatic. However, if symptoms occur, they tend to develop abruptly over a few minutes, including sudden shortness of breath or breathlessness with or without a cough or wheezing, rapid breathing, anxiety, and restlessness. Often at the time of pulmonary embolism, high blood pressure exists within the pulmonary arterial vasculature. If this is the case, when the embolism occurs, dull chest pain may occur. In a massive pulmonary embolism, right heart failure may develop with fluid in the abdominal and lower extremities. There may be light-headedness, unconsciousness, and seizures due to a drop in cardiac output from the failing heart.

In order to treat and/or prevent thrombosis several substances may be administered. Coumadin (warfarin), for instance, inhibits the synthesis of vitamin K-dependent coagulation factors such as Factors II, VII, IX and X and anticoagulant proteins C and S. Another agent used to prevent and treat thrombosis acetylsalicylic acid which inhibits platelet aggregation by interfering with thromboxane synthesis. Ticlopidine (Ticlid) inhibits platelet aggregation by interfering with the binding of fibrinogen to the platelet membrane. Ticlopidine is often considered in patients that have a high risk of thrombotic stroke and are intolerant to aspirin. Heparin (administered intravenously) increases the activity of antithrombin III, which prevents the conversion of fibrinogen to fibrin. Heparin is not absorbed by the gastrointestinal tract and must be administered intravenously. It is usually only used in emergency situations (e.g. after a stroke). Tissue plasminogen factor (t-PA) activates plasmin which breaks apart fibrin. t-PA is used in emergency situations to dissolve blood clots. Streptokinase is another tissue plasminogen factor drug. Both of these drugs are administered intravenously in emergency thrombotic situations (e.g. ischemic stroke).

It was surprisingly found that thrombi not only comprise fibrin, but also cytokeratins, in particular cytokeratin-18 or fragments thereof. Since cytokeratins are involved in the formation of thrombi the use of compounds degrading cytokeratins allows to dissolve said thrombi alone or in combination with other compounds regularly involved in thrombolytic therapy.

According to a preferred embodiment of the present invention the compound degrading CK-18 (or further degrading CK-18 fragments) is a protease preferably selected from the following list.

Especially preferred compounds are proteases (EC 3.4), in particular aminopeptidases (EC 3.4.11), dipeptidases (EC 3.4.13), dipeptidyl-peptidases and tripeptidyl-peptidases (EC 3.4.14), peptidyl-dipeptidases (EC 3.4.15), serine-type carboxypeptidases (EC 3.4.16), metallocarboxypeptidases (EC 3.4.17), cysteine-type carboxypeptidases (EC 3.4.18), omega peptidases (EC 3.4.19), serine endopeptidases (EC 3.4.21), cysteine endopeptidases (EC 3.4.22), aspartic endopeptidases (EC 3.4.23), metalloendopeptidases (EC 3.4.24) and threonine endopeptidases (EC 3.4.25).

Preferred aminopeptidases used according to the present invention are selected from the group consisting of leucyl aminopeptidase (EC 3.4.11.1), membrane alanyl aminopeptidase (EC 3.4.11.2), cystinyl aminopeptidase (EC 3.4.11.3), tripeptide aminopeptidase (EC 3.4.11.4), prolyl aminopeptidase (EC 3.4.11.5), arginyl aminopeptidase (EC 3.4.11.6), glutamyl aminopeptidase (EC 3.4.11.7), Xaa-Pro aminopeptidase (EC 3.4.11.9), bacterial leucyl aminopeptidase (EC 3.4.11.10), clostridial aminopeptidase (EC 3.4.11.13), cytosol alanyl aminopeptidase (EC 3.4.11.14), lysyl aminopeptidase (EC 3.4.11.15), Xaa-Trp aminopeptidase (EC 3.4.11.16), tryptophanyl aminopeptidase (EC 3.4.11.17), methionyl aminopeptidase (EC 3.4.11.18), D-stereospecific aminopeptidase (EC 3.4.11.19), aminopeptidase Ey (EC 3.4.11.20), aspartyl aminopeptidase (EC 3.4.11.21), aminopeptidase I (EC 3.4.11.22) and PepB aminopeptidase (EC 3.4.11.23).

Preferred dipeptidases used according to the present invention are selected from the group consisting of Xaa-His dipeptidase (EC 3.4.13.3), Xaa-Arg dipeptidase (EC 3.4.13.4), Xaa-methyl-His dipeptidase (EC 3.4.13.5), Glu-Glu dipeptidase (EC 3.4.13.7), Xaa-Pro dipeptidase (EC 3.4.13.9), Met-Xaa dipeptidase (EC 3.4.13.12), non-stereospecific dipeptidase (EC 3.4.13.17), cytosol nonspecific dipeptidase (EC 3.4.13.18), membrane dipeptidase (EC 3.4.13.19), b-Ala-His dipeptidase (EC 3.4.13.20) and dipeptidase E (EC 3.4.13.21).

Preferred dipeptidyl-peptidases and tripeptidyl-peptidases used according to the present invention are selected from the group consisting of dipeptidyl-peptidase I (EC 3.4.14.1), dipeptidyl-peptidase II (EC 3.4.14.2), dipeptidyl-peptidase III (EC 3.4.14.4), dipeptidyl-peptidase IV (EC 3.4.14.5), dipeptidyl-dipeptidase (EC 3.4.14.6), tripeptidyl-peptidase I (EC 3.4.14.9), tripeptidyl-peptidase II (EC 3.4.14.10) and Xaa-Pro dipeptidyl-peptidase (EC 3.4.14.11).

Preferred peptidyl-dipeptidases used according to the present invention are selected from the group consisting of peptidyl-dipeptidase A (EC 3.4.15.1), peptidyl-dipeptidase B (EC 3.4.15.4) and peptidyl-dipeptidase Dcp (EC 3.4.15.5).

Preferred serine-type carboxypeptidases used according to the present invention are selected from the group consisting of lysosomal Pro-Xaa carboxypeptidase (C 3.4.16.2), serine-type D-Ala-D-Ala carboxypeptidase (EC 3.4.16.4), carboxypeptidase C (EC 3.4.16.5) and carboxypeptidase D (EC 3.4.16.6).

Preferred metallocarboxypeptidases used according to the present invention are selected from the group consisting of carboxypeptidase A (EC 3.4.17.1), carboxypeptidase B (EC 3.4.17.2), lysine carboxypeptidase (EC 3.4.17.3), Gly-Xaa carboxypeptidase (EC 3.4.17.4), alanine carboxypeptidase (EC 3.4.17.6), muramoylpentapeptide carboxypeptidase (EC 3.4.17.8), carboxypeptidase E (EC 3.4.17.10), glutamate carboxypeptidase (EC 3.4.17.11), carboxypeptidase M (EC 3.4.17.12), muramoyltetrapeptide carboxypeptidase (EC 3.4.17.13), zinc D-Ala-D-Ala carboxypeptidase (EC 3.4.17.14), carboxypeptidase A2 (EC 3.4.17.15), membrane Pro-Xaa carboxypeptidase (EC 3.4.17.16), tubulinyl-Tyr carboxypeptidase (EC 3.4.17.17), carboxypeptidase T (EC 3.4.17.18), carboxypeptidase Taq (EC 3.4.17.19), carboxypeptidase U (EC 3.4.17.20), glutamate carboxypeptidase II (EC 3.4.17.21) and metallocarboxypeptidase D (EC 3.4.17.22).

A preferred cysteine-type carboxypeptidase used according to the present invention is cathepsin X (EC 3.4.18.1).

Preferred omega peptidases used according to the present invention are selected from the group consisting of acylaminoacyl-peptidase (EC 3.4.19.1), peptidyl-glycinamidase (EC 3.4.19.2), pyroglutamyl-peptidase I (EC 3.4.19.3), b-aspartyl-peptidase (EC 3.4.19.5), pyroglutamyl-peptidase II (EC 3.4.19.6), N-formylmethionyl-peptidase (EC 3.4.19.7), g-glutamyl hydrolase (EC 3.4.19.9), g-D-glutamyl-meso-diaminopimelate peptidase I (EC 3.4.19.11) and ubiquitinyl hydrolase 1 (EC 3.4.19.12).

Preferred serine endopeptidases used according to the present invention are selected from the group consisting of chymotrypsin (EC 3.4.21.1), chymotrypsin C (EC 3.4.21.2), metridin (EC 3.4.21.3), trypsin (EC 3.4.21.4), thrombin (EC 3.4.21.5), coagulation factor Xa (EC 3.4.21.6), plasmin (EC 3.4.21.7), enteropeptidase (EC 3.4.21.9), acrosin (EC 3.4.21.10), a-Lytic endopeptidase (EC 3.4.21.12), glutamyl endopeptidase (EC 3.4.21.19), cathepsin G (EC 3.4.21.20), coagulation factor VIIa (EC 3.4.21.21), coagulation factor IXa (EC 3.4.21.22), cucumisin (EC 3.4.21.25), prolyl oligopeptidase (EC 3.4.21.26), coagulation factor XIa (EC 3.4.21.27), brachyurin (EC 3.4.21.32), plasma kallikrein (EC 3.4.21.34), tissue kallikrein (EC 3.4.21.35), pancreatic elastase (EC 3.4.21.36), leukocyte elastase (EC 3.4.21.37), coagulation factor XIIa (EC 3.4.21.38), chymase (EC 3.4.21.39), complement subcomponent C (EC 3.4.21.41), complement subcomponent C (EC 3.4.21.42), classical-complement-pathway C3/C5 convertase (EC 3.4.21.43), complement factor I (EC 3.4.21.45), complement factor D (EC 3.4.21.46), alternative-complement-pathway C3/C5 convertase (EC 3.4.21.47), cerevisin (EC 3.4.21.48), hypodermin C (EC 3.4.21.49), lysyl endopeptidase (EC 3.4.21.50), endopeptidase La (EC 3.4.21.53), g-renin (EC 3.4.21.54), venombin AB (EC 3.4.21.55), leucyl endopeptidase (EC 3.4.21.57), tryptase (EC 3.4.21.59), scutelarin (EC 3.4.21.60), kexin (EC 3.4.21.61), subtilisin (EC 3.4.21.62), oryzin (EC 3.4.21.63), endopeptidase K (EC 3.4.21.64), thermomycolin (EC 3.4.21.65), thermitase (EC 3.4.21.66), endopeptidase So (EC 3.4.21.67), t-plasminogen activator (EC 3.4.21.68), protein C (activated) (EC 3.4.21.69), pancreatic endopeptidase E (EC 3.4.21.70), pancreatic elastase II (EC 3.4.21.71), IgA-specific serine endopeptidase (EC 3.4.21.72), u-plasminogen activator (EC 3.4.21.73), venombin A (EC 3.4.21.74), furin (EC 3.4.21.75), myeloblastin (EC 3.4.21.76), semenogelase (EC 3.4.21.77), granzyme A (EC 3.4.21.78), granzyme B (EC 3.4.21.79), streptogrisin A (EC 3.4.21.80), streptogrisin B (EC 3.4.21.81), glutamyl endopeptidase II (EC 3.4.21.82), oligopeptidase B (EC 3.4.21.83), limulus clotting factor (EC 3.4.21.84), limulus clotting factor (EC 3.4.21.85), limulus clotting enzyme (EC 3.4.21.86), omptin (EC 3.4.21.87), repressor LexA (EC 3.4.21.88), signal peptidase I (EC 3.4.21.89), togavirin (EC 3.4.21.90), flavivirin (EC 3.4.21.91), endopeptidase Clp (EC 3.4.21.92), proprotein convertase 1 (EC 3.4.21.93), proprotein convertase 2 (EC 3.4.21.94), snake venom factor V activator (EC 3.4.21.95), lactocepin (EC 3.4.21.96), assemblin (EC 3.4.21.97), hepacivirin (EC 3.4.21.98), spermosin (EC 3.4.21.99), pseudomonalisin (EC 3.4.21.100), xanthomonalisin (EC 3.4.21.101), C-terminal processing peptidase (EC 3.4.21.102), physarolisin (EC 3.4.21.103), mannan-binding lectin-associated serine protease-2 (EC 3.4.21.104) and rhomboid protease (EC 3.4.21.105).

Preferred cysteine endopeptidases used according to the present invention are selected from the group consisting of cathepsin B (EC 3.4.22.1), papain (EC 3.4.22.2), ficain (EC 3.4.22.3), chymopapain (EC 3.4.22.6), asclepain (EC 3.4.22.7), clostripain (EC 3.4.22.8), streptopain (EC 3.4.22.10), actinidain (EC 3.4.22.14), cathepsin L (EC 3.4.22.15), cathepsin H (EC 3.4.22.16), cathepsin T (EC 3.4.22.24), glycyl endopeptidase (EC 3.4.22.25), cancer procoagulant (EC 3.4.22.26), cathepsin S (EC 3.4.22.27), picornain 3C (EC 3.4.22.28), picornain 2A (EC 3.4.22.29), caricain (EC 3.4.22.30), ananain (EC 3.4.22.31), stem bromelain (EC 3.4.22.32), fruit bromelain (EC 3.4.22.33), legumain (EC 3.4.22.34), histolysain (EC 3.4.22.35), caspase-1 (EC 3.4.22.36), gingipain R (EC 3.4.22.37), cathepsin K (EC 3.4.22.38), adenain (EC 3.4.22.39), bleomycin hydrolase (EC 3.4.22.40), cathepsin F (EC 3.4.22.41), cathepsin 0 (EC-3.4.22.42), cathepsin V (EC 3.4.22.43), nuclear-inclusion-a endopeptidase (EC 3.4.22.44), helper-component proteinase (EC 3.4.22.45), L-peptidase (EC 3.4.22.46), gingipain K (EC 3.4.22.47), staphopain (EC 3.4.22.48), separase (EC 3.4.22.49), V-cath endopeptidase (EC 3.4.22.50), cruzipain (EC 3.4.22.51), calpain-1 (EC 3.4.22.52) and calpain-2 (EC 3.4.22.53).

Preferred aspartic endopeptidases used according to the present invention are selected from the group consisting of pepsin A (EC 3.4.23.1), pepsin B (EC 3.4.23.2), gastricsin (EC 3.4.23.3), chymosin (EC 3.4.23.4), cathepsin D (EC 3.4.23.5), nepenthesin (EC 3.4.23.12), renin (EC 3.4.23.15), HIV-1 retropepsin (EC 3.4.23.16), Pro-opiomelanocortin converting enzyme (EC 3.4.23.17), aspergillopepsin I (EC 3.4.23.18), aspergillopepsin II (EC 3.4.23.19), penicillopepsin (EC 3.4.23.20), rhizopuspepsin (EC 3.4.23.21), endothiapepsin (EC 3.4.23.22), mucorpepsin (EC 3.4.23.23), candidapepsin (EC 3.4.23.24), saccharopepsin (EC 3.4.23.25), rhodotorulapepsin (EC 3.4.23.26), acrocylindropepsin (EC 3.4.23.28), polyporopepsin (EC 3.4.23.29), pycnoporopepsin (EC 3.4.23.30), scytalidopepsin A (EC 3.4.23.31), scytalidopepsin B (EC 3.4.23.32), cathepsin E (EC 3.4.23.34), barrierpepsin (EC 3.4.23.35), signal peptidase II (EC 3.4.23.36), plasmepsin I (EC 3.4.23.38), plasmepsin II (EC 3.4.23.39), phytepsin (EC 3.4.23.40), yapsin 1 (EC 3.4.23.41), thermopsin (EC 3.4.23.42), prepilin peptidase (EC 3.4.23.43), nodavirus endopeptidase (EC 3.4.23.44), memapsin 1 (EC 3.4.23.45), memapsin 2 (EC 3.4.23.46), HIV-2 retropepsin (EC 3.4.23.47) and plasminogen activator Pla (EC 3.4.23.48).

Preferred metalloendopeptidases used according to the present invention are selected from the group consisting of atrolysin A (EC 3.4.24.1), microbial collagenase (EC 3.4.24.3), leucolysin (EC 3.4.24.6), interstitial collagenase (EC 3.4.24.7), neprilysin (EC 3.4.24.11), envelysin (EC 3.4.24.12), IgA-specific metalloendopeptidase (EC 3.4.24.13), procollagen N-endopeptidase (EC 3.4.24.14), thimet oligopeptidase (EC 3.4.24.15), neurolysin (EC 3.4.24.16), stromelysin 1 (EC 3.4.24.17), meprin A (EC 3.4.24.18), procollagen C-endopeptidase (EC 3.4.24.19), peptidyl-Lys metalloendopeptidase (EC 3.4.24.20), astacin (EC 3.4.24.21), stromelysin 2 (EC 3.4.24.22), matrilysin (EC 3.4.24.23), gelatinase A (EC 3.4.24.24), vibriolysin (EC 3.4.24.25), pseudolysin (EC 3.4.24.26), thermolysin (EC 3.4.24.27), bacillolysin (EC 3.4.24.28), aureolysin (EC 3.4.24.29), coccolysin (EC 3.4.24.30), mycolysin (EC 3.4.24.31), b-lytic metalloendopeptidase (EC 3.4.24.32), peptidyl-Asp metalloendopeptidase (EC 3.4.24.33), neutrophil collagenase (EC 3.4.24.34), gelatinase B (EC 3.4.24.35), leishmanolysin (EC 3.4.24.36), saccharolysin (EC 3.4.24.37), gametolysin (EC 3.4.24.38), deuterolysin (EC 3.4.24.39), serralysin (EC 3.4.24.40), atrolysin B (EC 3.4.24.41), atrolysin C (EC 3.4.24.42), atroxase (EC 3.4.24.43), atrolysin E (EC 3.4.24.44), atrolysin F (EC 3.4.24.45), adamalysin (EC 3.4.24.46), horrilysin (EC 3.4.24.47), ruberlysin (EC 3.4.24.48), bothropasin (EC 3.4.24.49), bothrolysin (EC 3.4.24.50), ophiolysin (EC 3.4.24.51), trimerelysin I (EC 3.4.24.52), trimerelysin II (EC 3.4.24.53), mucrolysin (EC 3.4.24.54), pitrilysin (EC 3.4.24.55), insulysin (EC 3.4.24.56), O-sialoglycoprotein endopeptidase (EC 3.4.24.57), russellysin (EC 3.4.24.58), mitochondrial intermediate peptidase (EC 3.4.24.59), dactylysin (EC 3.4.24.60), nardilysin (EC 3.4.24.61), magnolysin (EC 3.4.24.62), meprin B (EC 3.4.24.63), mitochondrial processing peptidase (EC 3.4.24.64), macrophage elastase (EC 3.4.24.65), choriolysin L (EC 3.4.24.66), choriolysin H (EC 3.4.24.67), tentoxilysin (EC 3.4.24.68), bontoxilysin (EC 3.4.24.69), oligopeptidase A (EC 3.4.24.70), endothelin-converting enzyme (EC 3.4.24.71), fibrolase (EC 3.4.24.72), jararhagin (EC 3.4.24.73), fragilysin (EC 3.4.24.74), lysostaphin (EC 3.4.24.75), flavastacin (EC 3.4.24.76), snapalysin (EC 3.4.24.77), gpr endopeptidase (EC 3.4.24.78), pappalysin-1 (EC 3.4.24.79), membrane-type matrix metalloproteinase-1 (EC 3.4.24.80), ADAM10 endopeptidase (EC 3.4.24.81), ADAMTS-4 endopeptidase (EC 3.4.24.82), anthrax lethal factor endopeptidase (EC 3.4.24.83), Step 24 endopeptidase (EC 3.4.24.84), S2P endopeptidase (EC 3.4.24.85) and ADAM 17 endopeptidase (EC 3.4.24.86).

A preferred threonine endopeptidase used according to the present invention is proteasome endopeptidase complex (EC 3.4.25.1).

Particularly preferred proteasome for degradation of CK-18 or fragments thereof is Kallikrein 8 (see e.g. Santin A. D. et al (2004), Ganecol. Oncol. 94:283-288). More specifically, Kallikrein 7 and 8 as well as mast cell chymase are preferred proteases to be used according to the present invention.

According to a preferred embodiment of the present invention the medicament further comprises warfarin, acetylsalicylic acid, ticlopidine, heparin, tissue plasminogen factor (t-PA), streptokinase, and/or urokinase.

BRIEF DESCRIPTION OF THE DRAWINGS

The present invention is further illustrated in the following figures and examples, however, without being restricted thereto.

FIG. 3A shows a hematoxylin-eosin staining; FIG. 3B an acid-fuchsin orange G staining (fibrin—red, erythrocytes, thrombocytes and other plasma-proteins—orange, scattered leucocytes—blue); FIG. 3C positive immunoreactivity of CK-18 M30- neo-epitope in the centre of the thrombus; FIG. 3D a negative control (all magnification ×200).

EXAMPLE

Figure 1:
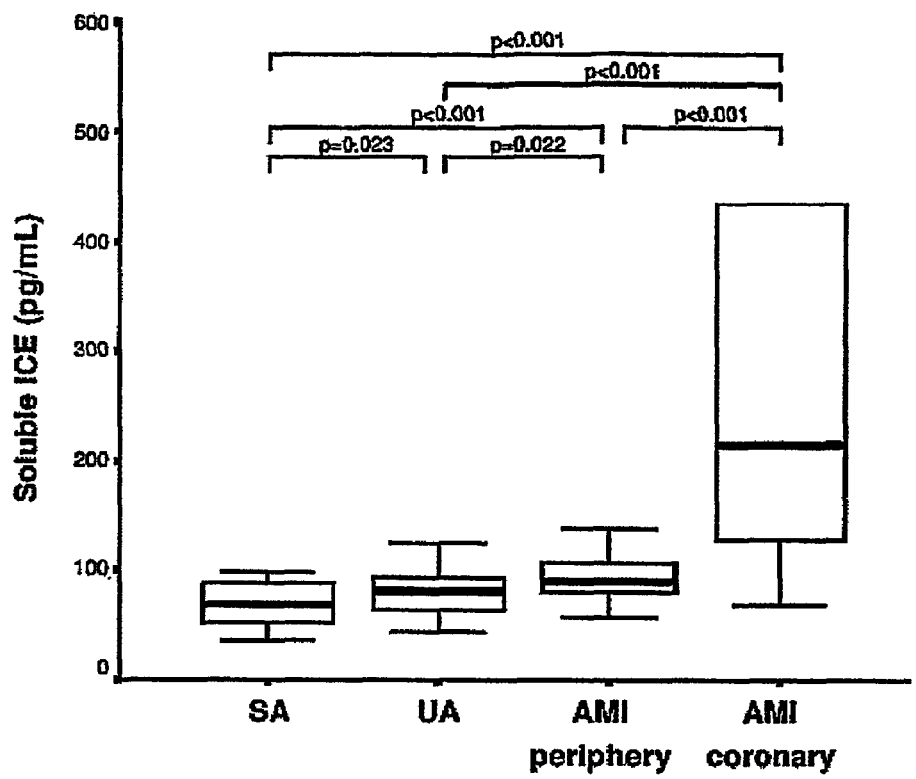
FIG. 1 shows plasma levels of soluble interleukin-1 converting enzyme/ICE. The concentration of sICE in plasma of 40 patients with stable angina (SA), unstable angina (UA) was compared to plasma obtained from the femoral artery and coronary artery in acute myocardial infarction (AMI). Each box represents the inter quartile containing the 50% values. The line across the box indicates the median line. The whiskers extend from the box to the highest and lowest values.

In this example the expression of proteins known to be associated with inflammatory and apoptosis-specific activation pathways in AMI was investigated. The concentration of said proteins in the plasma obtained at the coronary artery system in patients suffering of AMI was determined and related to systemic blood levels. Patients diagnosed with UA and stable angina (SA) served as controls in a non-randomized, comparative study. Furthermore, the in vivo obtained acute coronary thrombus was analyzed by immunohistochemistry. The results evidence increased concentrations of apoptosis-specific ICE and the caspase-dependent cleavage product CK-18 in AMI as compared to SA and UA.

Systemic inflammation and apoptosis-specific immune activation play a major role in acute coronary syndromes (ACS), including acute myocardial infarction (AMI). Thrombectomy devices were recently introduced in the clinical arena to allow removal of intracoronary thrombotic material in the setting of AMI. This technique offers the unique possibility to harvest blood and thrombus at the occluded coronary artery and femoral artery in order to compare inflammatory and apoptosis-specific proteins. Patients with stable (SA) and unstable angina (UA) served as control population.

Patients and Clinical Features

Forty consecutive patients undergoing emergency coronary angiography were included in the study, if they met the following criteria: 1) chest pain at the time of coronary angiography, 2) new ST-segment elevations≧2 mm in two or more chest leads, or new ST-segment elevations≧1 mm in more than one horizontal plane lead observed within 20 min of coronary angiography, 3) coronary anatomy suitable for X-sizer thrombectomy, 4) no thrombolytic therapy, 5) visible thrombus material in the X-sizer filter and bottle unit indicating successful thrombectomy and 6) written informed consent. Criteria for the use of the X-sizer were a vessel diameter≧3 mm, a large intraluminal contrast defect suggestive of thrombus within 50 mm of the respective ostium, with TIMI 0-1 flow after passage of the angiographic guide wire, in the absence of severe vessel tortuosity, calcification or difficult vascular access In addition, eighty consecutive patients admitted to the institution for the assessment of angina chest pain had undergone coronary angiography and served as controls. SA (n=40) was defined by typical exertional chest pain angina relieved by rest, glyceryl trinitrate administration, or both with positive response to exercise ECG stress testing and ≧50% diameter stenosis in ≧1 coronary artery at catheterization. Patients with UA (n=40) were defined according to the criteria of Braunwald.24 All patients with UA class IIIB had diagnostic ST segment changes, T wave inversion, or both. No patient included in the study had evidence of ongoing systemic or cardiac inflammatory process as defined by clinical history. Table 1 summarizes demographic and baseline clinical characteristics.

TABLE 1

Characteristics of study patients

| | SA (n = 40) | UA (n = 40) | AMI (n = 40) |
|---|---|---|---|
| Men/women | 30 (75%)/ 10 (25%) | 28 (70%)/ 12 (30%) | 28 (70%)/ 12 (30%) |
| Mean age (years) | 62.1 ± 11.6 | 63.1 ± 13.5 | 59.3 ± 10.1 |
| History and risk factors | | | |
| Previous CABG | 5 (12.5%) | 7 (17.5%) | 6 (15%) |
| Previous PTCA | 16 (40%) | 13 (32.5%) | 6 (15%) |
| IDDM | 1 (2.5%) | 1 (2.5%) | 5 (12.5%) |
| NIDDM | 5 (12.5%) | 6 (15%) | 4 (10%) |
| Hypertension | 25 (62.5%) | 25 (62.5%) | 25 (62.5%) |
| Current smoker | 14 (35%) | 15 (37.5%) | 21 (52.5%) |
| Former smoker | 12 (30%) | 12 (30%) | 5 (12.5%) |
| Never smoked | 24 (60%) | 23 (57.5%) | 13 (32.5%) |
| Angiographic analysis | | | |
| One vessel disease | 10 (25%) | 12 (30%) | 21 (52.5%) |
| Two vessel disease | 16 (40%) | 15 (37.5%) | 9 (22.5%) |
| Three vessel disease | 14 (35%) | 13 (32.5%) | 10 (25%) |
| Left ventricular systolic function | | | |
| Normal | 28 (70%) | 30 (75%) | 19 (47.5%) |
| Mild impairment | 9 (22.5%) | 5 (12.5%) | 8 (20%) |
| Moderate impairment | 3 (7.5%) | 5 (12.5%) | 8 (20%) |
| Severe impairment | 0 (0%) | 0 (0%) | 5 (12.5%) |
| Biochemistry (mean) | | | |
| Cholesterol (mg/dL) | 199 ± 52 | 204 ± 52 | 206 ± 45 |
| LDL cholesterol (mg/dL) | 126 ± 43 | 133 ± 44 | 125 ± 44 |
| HDL cholesterol (mg/dL) | 45 ± 15 | 41 ± 12 | 48 ± 26 |
| Triglyceride (mg/dL) | 182 ± 109 | 203 ± 111 | 205 ± 208 |
| Creatinine (mg/dL) | 1.1 ± 0.2 | 1.1 ± 0.2 | 1.1 ± 0.4 |
| CRP (mg/dL) | 0.8 ± 0.76 | 1.8 ± 2.8* | 3.6 ± 6.1 |
| Leukocytes (×1000/dL) | 7.5 ± 1.9 | 9.2 ± 3.4† | 9.8 ± 3.4 |

Data are mean ± SD unless stated otherwise. SA: stable angina; UA: unstable angina; AMI: acute myocardial infarction; CABG: coronary artery bypass grafting; PTCA: percutaneous transluminal coronary angioplasty; IDDM: insulin-dependent diabetes mellitus; NIDDM: non-insulin dependent diabetes mellitus; LDL: low density lipoprotein; HDL: high density lipoprotein; CRP: C-reactive protein; NA: not available.
*CRP: SA vs. UA p = 0.047
†Leukocytes: SA vs. UA p = 0.017

Collection and Processing of Samples

Patients were heparinized at an activated coagulation time≧300 s and 250 mg of aspirin. Whole blood samples were retrieved from the femoral artery into citrate-vacutainers, immediately centrifuged (1300×g, 4° C., 10 min) and served as internal controls to blood samples obtained directly from the occluded coronary artery. Platelet poor plasma was frozen at −80° C. until the assays. The X-sizer thrombectomy catheter system (EndiCOR Medical Inc) consists of a dual-lumen catheter shaft connected to a handheld control module. The inner lumen contains a helical cutter rotated at ~2.100 rpm increasing suction on the thrombus in addition to vacuum through the outer lumen (see FIG. 1).

A few centimeters before the vacuum-glass bottle, the aspirate passes a small filter unit in which thrombotic material and plaque particles are trapped, while blood is aspirated into the heparinized glass bottle. Blood was immediately transferred into citrate-vacutainers and centrifuged as described above. The thrombus material tapped in the filter unit was fixed in 7.5% buffered formalin over night, embedded in paraffin, and serial 3 µm microtom-sections were performed. The blood sucked by the vacuum lumen was immediately transferred into citrate-vacutainers and procoagulant as described above. Samples were frozen immediately at −80° C.

Quantification of Soluble IL-1βp, IL-1β, TNF-α, TNF-R1, CD40, and CD40L

Protein concentrations were measured by ELISA, purchased by BenderMedSystems (Austria) and MBL International (USA). TNF-α levels were detected by a high-sensitivity ELISA (BenderMedSystems, Austria). The assays were run following the manufacturers' instructions. In short, plates were either precoated or coated with a supplied coating antibody, sealed and incubated over night at 4° C. Plates were washed (0.5 mL Tween20 ad 1 L PBS) and blocked with assay buffer (5 g BSA; 0.5 ml Tween20 ad 1 L PBS) for two h at room temperature. Then they were washed again and a biotin conjugate was added to each well. Plates were further incubated for two h, washed, and incubated with streptavidin-horseradish peroxidase (HRP)/conjugate. After 1 h of treatment and additional washing step, TMB substrate solution (Sigma-Aldrich, St. Louis, Mich., USA) was added. When color development was evident the reaction was terminated with 1N sulphuric acid. Plates were read at 450 nm on a Wallac Multilabel counter 1420 (PerkinElmer, USA).

Quantification of Soluble ICE

A commercial ELISA, provided by BenderMedSystems (Austria), was used to measure ICE. The ICE ELISA detects both the p45 precursor and the enzymatically active p10:p20 complex. Interaction between ICE and its precursor substrate occurs exclusively inside the cell. Samples and standards were diluted in provided assay diluent. Plates were incubated for two h and washed three times. After another incubation period with a second antibody and washing step the HRP-conjugated detection antibody was added. Plates were incubated for 30 min on a rotator set. Then they were emptied and washed before the TMB substrate solution (Sigma-Aldrich) was added. The color reaction was stopped with 1N sulphuric acid and subjected to measurement on a Wallac Multilabel counter 1420 (PerkinElmer) at a wave length of 450 nm.

Quantification of Cytokeratin 18 M30-Neo-Epitope

Circulating CK-18 M30-neo-epitope was measured by ELISA, purchased from PEVIVA AB (Bromma, Sweden). This ELISA uses a monoclonal antibody recognizing an epitope on the 238-396 fragment of CK-18 as catcher, and HRP-conjugated M30 as detector. M30 antigen levels are expressed in units/L. One unit corresponds to 1.24 µmol of a synthesized peptide containing the M30 recognition motif according to the manufacturer. The sensitivity of the ELISA is 30 U/L. The intra- and interassay coefficients of variation of the CK-18 ELISA were 0.7-5.8% and 2.8-4.8%, respectively. The amount of protein in each sample was calculated according to a standard curve of optical density-values constructed for known levels of CK-18 neoepitope M30. (Leers M P, Kolgen W, Bjorklund V, et al., J Pathol 1999; 187(5):567-72

Immunohistochemistry

For detection of apoptosis a mononclonal mouse antibody against M30 neo-epitope25 was used. Fresh thrombi from patients with AMI were fixed in 7.5% buffered formalin and embedded in paraffin. Consecutive, 3 µm sections were stained with hematoxylin and acid-fuchsin orange G (trichrome stain). For immunostaining, microwave pretreatment in citrate buffer (2×5 min, 600 W) was applied. To avoid unspecific staining, samples were treated with 5% BSA (Sigma-Aldrich/tris buffered saline (TBS) for 30 min. Afterwards, the slides were incubated with the primary antibody (1:50, anti-M30 antibody, Roche, Germany) overnight at room temperature. This was followed by incubation with biotin-labeled mouse antibody (1:100, Vector Laboratories, Bulingame, Calif., USA) for 1 h and detection by alkaline phosphatase-conjugated streptavidine-AP/10% human serum (1:100, Dako, Denmark). Visualization was achieved with fast red (Sigma, USA). For negative controls, primary antibodies were substituted by irrelevant mouse IgG.

Statistical Analysis

Results are presented as mean±SEM, if not otherwise mentioned. Due to the relatively small sample size, the Mann-Whitney U test was used to calculate significance. A p value 0.05 was deemed to be significant.

Results

Demographic and some baseline characteristics of patients are depicted in table 1. In both SA and UA study groups, a similar number of patients had a history of myocardial infarction or previous coronary intervention (coronary artery bypass graft or percutaneous transluminal coronary angioplasty). Established risk factors for coronary artery disease, total cholesterol concentrations and angiographic findings were similar in both groups.

The AMI group included 40 patients, 28 men (70%) and 12 women (30%). Mean age was 59.3 years. 30% of the patients had pri- or revascularization therapy by either PCI or bypass surgery. Nine (22.5%) of the present study patients suffered from diabetes, 25 (62.5%) from hypertension and 21 (52.5%) were current smokers. Average cholesterol levels were 206.3 mg/dL (ULN=199 mg/dL) and triglycerides were 204.6 mg/dL (ULN=172 mg/dL). Mean C-reactive protein levels were 3.6 mg/dL (ULN=1 mg/dL) indicating a systemic inflammatory process. Nineteen (47.5%) suffered from two- or three-vessel disease. In only one patient the left main artery was involved. More than half of the patients (52.5%) showed reduced left ventricular function identified by echocardiography.

Inflammatory and Apoptosis-Specific Proteins

To investigate if systemic inflammatory response syndrome is mimicked at the site of AMI as compared to SA and UA, plasma samples were obtained by X-sizer and evaluated. Plasma samples obtained from the femoral artery in patients suffering from AMI served as internal controls. Derivatives of inflammatory cytokines (IL-1βp, IL-1β, TNF-α, TNF-R1, sCD40 and CD40L) and their significances are delineated in table 2.

TABLE 2

Plasma levels of cytokines and other soluble membrane proteins in SA, UA and AMI

| | SA (n = 40) | UA (n = 4) | AMI periphery (n = 40) | AMI coronary (n = 40) |
| --- | --- | --- | --- | --- |
| IL-1β precursor (pg/mL) | 133.6 ± 14.01 | 92.02 ± 15.04* | 47.49 ± 13.58 | 44.41 ± 8.234* |
| IL-1β (pg/mL) | 27.42 ± 0.316 | 28.81 ± 0.862 | 29.03 ± 0.717 | 29.18 ± 0.547 |
| hs-TNF-α (pg/mL) | 15.87 ± 7.903 | 18.84 ± 7.769 | 17.59 ± 0.623 | 17.57 ± 0.682 |
| sTNF-R1 (ng/mL) | 0.43 ± 0.084 | 0.43 ± 0.058 | 1.46 ± 0.323‡ | 1.35 ± 0.304‡ |
| sCD40 (pg/mL) | 56.18 ± 6.808 | 49.5 ± 4.832 | 60.73 ± 2.597 | 62.5 ± 4.816 |
| sCD40L (pg/mL) | 721.8 ± 224 | 1078.2 ± 592 | 2005.4 ± 127.5 | 2149.2 ± 160.6† |

Data are mean ± SD unless slated otherwise. SA: stable angina; UA: unstable angina; AMI: acute myocardial infarction;
*IL-1β precursor: SA vs. UA p = 0.04; SA vs. AMI coronary artery p < 0.001; UA vs. AMI coronary artery p = 0.007
‡TNF-R1: SA vs. AMI coronary p = 0.005; UA vs. AMI periphery p = 0.002; UA vs. AMI coronary p = 0.005
†sCD40L: SA vs. AMI periphery p < 0.0001

Soluble ICE and CK-18

As depicted in FIG. 1 the mean plasma levels of soluble ICE were 68.6±20.2 in SA, 81.5±24.3 in UA, 96±27.1 in AMI femoral (periphery), and 282.2±180 in AMI coronary artery samples. This data evidence a significant increase in the concentration of ICE in the sample derived from the site of myocardial infarction as compared to the systemic blood level as well as SA and UA (SA vs UA p=0.023, UA vs AMI periphery p=0.022 and AMI periphery vs AMI coronary p<0.001)

Figure 2:
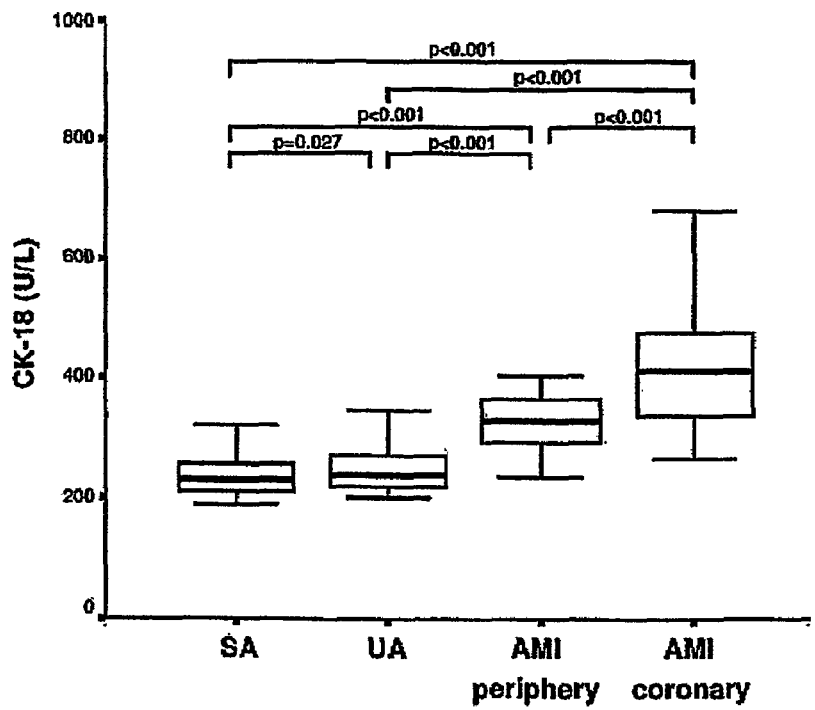
FIG. 2 shows plasma levels of cytokeratin 18 M30-neo-epitope in the acute myocardial infarction, SA and UA. The concentration of CK-18 M30-neo-epitope in the plasma obtained from patients coronary artery was markedly increased when compared to the systemic blood flow obtained from the femoral artery, UA and SA. The data obtained from 40 patients represent the inter quartile containing the 50% values. The line across the box indicates the median line. The whiskers extend from the box to the highest and lowest values.

The results depicted in FIG. 2 show a marked increase in the concentration of CK-18-M30 neoepitope in the plasma derived from the site of myocardial infarction compared to the periphery (411±15.3 vs 336.8±9.9, p=0.001). Further significant differences were found between AMI periphery and UA (336.8±9.9 vs 255±5, p<0.001), as well as UA and SA (255.5±8.9 vs 232.4±4.9, p=0.027).

Detection of CK-18 in the Thrombus Causing Myocardial infarction

Figure 3:
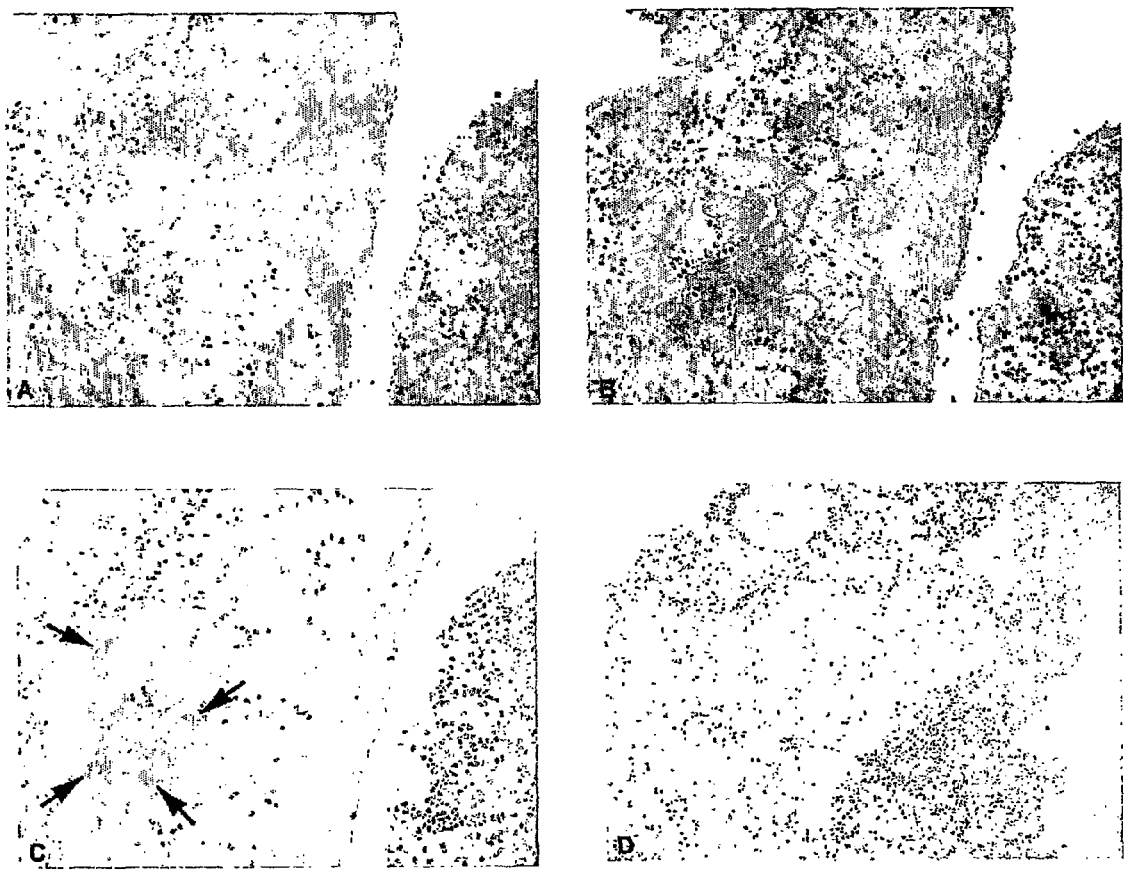
FIG. 3A to 3D show a representative thrombus from a patient with acute myocardial infarction (n=8).

Thrombi harvested by thrombectomy device were subjected to immunohistochemistry as well as routine hematoxilin-eosin (HE) and acid-fuchsin orange G staining. FIG. 3 (A,B,C,D) shows a representative thrombus (n=8) causing acute myocardial ischemia. Panel (A), representing the HE stain, contains pale areas which were identified in further immunohistochemestry to consist not only of fibrin but also significant amounts of the microfilament CK-18. Moreover, scattered leucocytes and erythrocytes can be observed. By immunohistochemical staining in the central portions of the thrombus CK-18 positive areas are detectable (panel C), which mainly correspond to areas rich of fibrin precipitates (see acid-fuchsin orange G staining, panel B). Panel D represents unspecific control stain for M30. Peripheral blood buffy coat served as internal controls.

Discussion

This example demonstrates that ICE, a member of the caspase family, is markedly increased at the site of acute coronary thrombosis in patients suffering of AMI, and only moderately in the periphery as well as in UA, as compared to SA. Interestingly, in patients with AMI, this finding is associated with elevated content of systemic microfilament CK-18, a product of specific caspase activation.

ICE/caspase-1, a protease with Cys285 serving as the catalytic residue, cleaves the 31 kDa biological inactive IL-1β precursor at Asp116-Ala117 to generate the 17.5 kDA mature form of IL-1β (Bombeli T, Karsan A, Tait J F, Harlan J M., Blood 1997; 89(7):2429-42) (Kostura M J, Tocci M J, Limjuco G, et al., Proc Natl Acad Sci USA 1989; 86(14):5227-31). The active enzyme consists of two nonidentical subunits (p10 and p20), both of which are essential for enzymatic activity, and therefore play a pivotal role in apoptosis of various cells including cardiomyocytes. Increased expression of ICE in cardiac hypertrophy, the over production of TNF-α in cardiomyopathy (Kubota T, Miyagishima M, Frye C S, et al., J Mol Cell Cardiol 2001; 33(7):1331-44), and endotoxin-induced myocardial dysfunction (Fauvel H, Marchetti P, Chopin C, Formstecher P, Neviere R., Am J Physiol Heart Circ Physiol 2001; 280(4):H1608-14) prompted the evaluation of presence of soluble ICE at the site of AMI. A mean 4.1 fold increase of ICE at the site of AMI was observed in comparison to UA. It is likely that under conditions of endotoxic or hypoxic stress caspase-1 is permitted to act synergistically with these physiological stressors and induce apoptosis via caspase-3. In an experimental model of ischemia and reperfusion injury IL-1 receptor antagonist gene transfection has been shown to reduce infarct size (Frantz S, Ducharme A, Sawyer D, et al., J Mol Cell Cardiol 2003; 35(6):685-94), and the increased myocardial levels of ICE may predispose to apoptotic myocardial injury under conditions of stress (Syed F M, Hahn H S, Odley A, et al., Circ Res 2005; 96(10):1103-9).

Cytokeratin 18, a major component of intermediate filaments, is widely expressed by epithelial tissues and in small amounts on fibroblasts and other non-epithelial cells (Schaafsma H E, Ramaekers F C., Pathol Annu 1994; 29 Pt 1:21-62). In apoptotic cells Cytokeratin 18 is phosphorylated, the main sites is on serine 53, and microfilaments aggregates rapidly (Ku N O, Liao J, Omary M B., J Biol Chem 1997; 272(52): 33197-203) (Caulin C, Salvesen G S, Oshima R G., J Cell Biol 1997; 138(6): 1379-94). Different stress conditions such as heat-shock stress and viral infection, may increase microfilament reorganization and solubility, and altered polymerization (Ku N O, Liao J, Omary M B., J Biol Chem 1997; 272(52):33197-203.) (Schutte B, Henfling M, Kolgen W, et al., Exp Cell Res 2004; 297(1):11-26). The phosphorylated CK-18 is a preferential substrate for proteolysis. The caspase-mediated cleavage of CK-18 during apoptosis (Caulin C, Salvesen G S, Oshima R G., J Cell Biol 1997; 138(6):1379-94) leads to formation of a specific neo-epitope, recognized by the antibody M30 (Leers M P, Kolgen W, Bjorklund V, et al., J Pathol 1999; 187(5):567-72) (Kadyrov M, Kaufmann P, Huppertz B., Placenta 2001; 22(1):44-8). Interestingly, a marked increase in the concentration of CK-18, neo-epitope M30, was measured in the plasma obtained directly from the site of myocardial infarction. Furthermore, the increased content of the CK-18 was corroborated by our finding that thrombectomy device obtained thrombus in AMI stained positive for CK-18. This novel feature of thrombus might serve as additional explanation why intravenous thrombolytic therapies aiming at fibrin lysis, only incompletely restores early and complete coronary flow in ≧50% of patients suffering of AMI (Valgimigli M, Merli E, Malagutti P, et al., Arch Biochem Biophys 2003; 420(2): 255-61.) (Topol E J. Toward, Circulation 1998; 97(2):211-8) (Rentrop K P., Circulation 2000; 101(13): 1619-26).

The CD40L/CD154 is a transmembrane-bound protein expressed by a variety of activated cells associated with disrupted atheroma, such as vascular endothelial cells, macrophages, T lymphocytes, smooth muscle cells, and platelets (Mach F, Schonbeck U, Sukhova G K, et al., Proc Natl Acad Sci USA 1997; 94(5):1931-6). This proinflammatory mediator can be cleaved from cell membranes to form sCD40L, which retains its biological property to interact with CD40 and initiates a varied inflammatory response (Mach. F, Schonbeck U, Sukhova G K, et al., Proc Natl Acad Sci USA 1997; 94(5):1931-6) (Aukrust P, Muller F, Ueland T, et al., Circulation 1999; 100(6):614-20). Enhanced levels of sCD40L have been previously found in patients with UA, (Aukrust P, Muller F, Ueland T, et al., Circulation 1999; 100(6):614-20) and myocardial infarction. (Ohashi Y, Kawashima S, Mori T, et al., Int J Cardiol 2005). In line with these findings the present results evidenced a significant increase of sCD40L at the site of acute myocardial infarction, as compared to SA.

It has been previously shown that the endothelial injury is an integral part in AMI and UA, (Mutin M, Canavy I, Blann A, Bory M, Sampol J, Dignat-George F., Blood 1999; 93(9): 2951-8) and serum from patients with UA is pro-apoptotic on human umbilical vein endothelial cells as compared with that from patients with SA (Valgimigli M, Agnoletti L, Curello S, et al., Circulation 2003; 107(2):264-70). Moreover, when the latter serum has been re-evaluated at a 1-year follow up, in stable clinical conditions, it was observed that they did not differ anymore from patients with stable lesions, suggesting that increased apoptotic activity of serum is temporally linked to UA.

Inflammatory processes both locally within atherosclerotic plaque and systemically, within the circulation, are established features in the pathogenesis of coronary heart disease (Braunwald E. Circulation 1989; 80(2):410-4). It has been suggested that apoptosis of endothelial cells covering atherosclerotic lesions may lead to plaque rupture and that release of tissue factor laden membrane microparticles by cells undergoing apoptosis could directly initiate the coagulation cascade. The technique of acute thrombectomy in myocardial infarction offers a unique possibility to harvest blood samples directly out of the culprit coronary artery at the time of the acute event and compare it to systemic blood. The data suggest that systemic activation of immunologic processes in interplay with particularly locally enhanced apoptosis is a key mechanism in AMI.

The present example is the first to report on elevated inflammatory/apoptosis-specific proteins at the site of acute coronary thrombosis as compared to peripheral blood in patients suffering of AMI. From previously studies it is known that AMI is a result of locally inflamed plaque followed by plaque rupture and subsequent thrombotic vessel occlusion and systemic inflammation (Mutin M, Canavy I, Blann A, Bory M, Sampol J, Dignat-George F., Blood 1999; 93(9):2951-8). The expression of proapoptotic genes like BAX, CASP1, FAS, p53 or PCNA was significantly higher in ACS plaques derived from directional coronary atherectomy, whereas anti-apoptotic genes, as MDM2 were more expressed in plaques from patients diagnosed with SA (Rossi M L, Marziliano N, Merlini P A, et al. Circulation 2004; 110(13):1767-73). Systemic inflammatory processes are including among others monocyte infiltration, neutrophil attraction and the expansion of plaque destabilizing CD4+ CD28– cells (Zal B, Kaski J C, Arno G, et al. Circulation 2004; 109(10):1230-5). These observations indicate that mechanisms underlying cell homeostasis and repair are active and more balanced in SA, whereas unstable plaques could be characterised by unbalanced programmed cell death resulting form the activation of pro-apoptotic genes. Moreover, it was reported that antibodies directed towards anti-60 kDa heat shock protein, cholesterol, Clamydia pneumonie, and CK-18 (Willseron J T. Prog. Cardiovasc Dis 2002; 44(6):569-78), are associated with ischemic heart disease.

Increased levels of ICE and CK-18 or fragments thereof, in addition to CD40L, are associated with clinical instability, and therefore may be considered as pathognomic features of acute coronary syndromes. This in vivo obtained information translates to trials including pharmacological use of caspase-inhibitors in prevention of cardiomyocyte apoptosis and myocardial infarct expansion (Yaoita H, Ogawa K, Maehara K, Maruyama Y. Circulation 1998; 97(3):276-81). Novel therapies targeting CK-18 or fragments thereof in AMI are warranted.

Summarizing, the X-sizer thrombectomy device was utilized in patients suffering from AMI (n=40). UA (n=40) and SA (n=40) were included as control populations. The inflammatory and apoptosis-specific proteins IL-1β precursor (IL-1βp), IL-1β, TNF-α, TNF-R1, CD40, CD40L, interleukin-1β-converting enzyme/ICE and the CK-18 were determined by ELISA. Immunohistochemistry was utilized to evaluate presence of CK-18 in coronary thrombus obtained from patients suffering from AMI. Group comparisons were evaluated by Mann-Whitney U test.

Soluble IL-1βp, ICE and CK-18 (or its fragments) were identified to be novel discriminators between SA and UA (p=0.034, p=0.023, p=0.027, respectively). Interestingly, soluble ICE and CK-18 were significantly increased at the site of myocardial infarction as compared to the systemic blood (both p=0.001), indicating a novel pathognomonic role in the acute event of myocardial infarction. This observation was corroborated by the finding that M30, an antibody able to identify CK-18, stained positive in the coronary thrombus causing myocardial infarction.

Acute myocardial infarction is related to increased systemic ICE and CK-18 levels in vivo.

The utilization of thrombectomy devices allows the removal of intracoronary thrombotic material which offers the unique possibility to harvest blood and thrombus and plasma at the occluded coronary artery and concomitantly at the femoral artery in order to compare inflammatory and apoptosis specific proteins. Patients with stable and unstable angina served as control (all groups, n=40). Group comparisons were evaluated by Mann Whitney U test.

The inflammatory and apoptosis specific proteins IL-1βp, IL-1β, hs-TNFα, TNF-R1, CD40, CD40L, interleukin-1β-converting enzyme/ICE and the CK-18 were determined by ELISA. Immunohistochemistry was utilized to evaluate presence of CK-18 in coronary thrombus obtained from patients suffering from acute myocardial infarction.

The novel information pertains to: Soluble IL-1βp, ICE and CK-18 were identified to be novel discriminators between stable and unstable angina (p=0.034, p=0.023, p=0.027, respectively).

Interestingly, IL-1β, hs-TNFα, TNF-R1, CD40 and CD40L did not meet any significance in the group unstable vs stable angina cohort. However, it has to be stated that CD40L concentration determined in the present example were comparable to the mean values determined in relevant literature.

Interestingly, ICE and CK-18 were significantly increased at the site of myocardial infarction as compared to the systemic blood in patients with acute myocardial infarction (both, p=0.0001). This indicates a novel pathognomonic role in the acute event of myocardial infarction. This observation was corroborated by the finding that M30, an antibody able to identify CK-18, stained positive in the thrombus causing myocardial infarction.

REFERENCES

1. Thornberry N A, Bull H G, Calaycay J R, et al. A novel heterodimeric cysteine protease is required for interleukin-1 beta processing in monocytes. Nature 1992; 356 (6372):768-74.
2. Mattey D L, Dawes P T, Nixon N B, Goh L, Banks M J, Kitas G D. Increased levels of antibodies to cytokeratin 18 in patients with rheumatoid arthritis and ischaemic heart disease. Arm Rheum Dis 2004; 63(4):420-5.
3. Bombeli T, Karsan A, Tait J F, Harlan J M. Apoptotic vascular endothelial cells become procoagulant. Blood 1997; 89(7):2429-42.
4. Leers M P, Kolgen W, Bjorklund V, et al. Immuhocytochemical detection and mapping of a cytokeratin 18 neo-epitope exposed during early apoptosis. J Pathol 1999; 187(5):567-72.
5. Kostura M J, Tocci M J, Limjuco G, et al. Identification of a monocyte specific pre-interleukin 1 beta convertase activity. Proc Natl Acad Sci USA 1989; 86(14):5227-31.
6. Kubota T, Miyagishima M, Frye C S, et al. Overexpression of tumor necrosis factor-alpha activates both anti- and pro-apoptotic pathways in the myocardium. J Mol Cell Cardiol 2001; 33(7):1331-44.

7. Fauvel H, Marchetti P, Chopin C, Formstecher P, Neviere R. Differential effects of caspase inhibitors on endotoxin-induced myocardial dysfunction and heart apoptosis. Am J Physiol Heart Circ Physiol 2001; 280(4):H1608-14.
8. Frantz S, Ducharme A, Sawyer D, et al. Targeted deletion of caspase-1 reduces early mortality and left ventricular dilatation following myocardial infarction. J Mol Cell Cardiol 2003; 35(6):685-94.
9. Syed F M, Hahn H S, Odley A, et al. Proapoptotic effects of caspase-1/interleukin-converting enzyme dominate in myocardial ischemia. Circ Res 2005; 96(10):1103-9.
10. Schaafsma H E, Ramaekers F C. Cytokeratin subtyping in normal and neoplastic epithelium: basic principles and diagnostic applications. Pathol Annu 1994; 29 Pt 1:21-62.
11. Ku N O, Liao J, Omary M B. Apoptosis generates stable fragments of human type I keratins. J Biol Chem 1997; 272(52):33197-203.
12. Caulin C, Salvesen G S, Oshima R G. Caspase cleavage of keratin 18 and reorganization of intermediate filaments during epithelial cell apoptosis. J Cell Biol 1997; 138(6): 1379-94.
13. Schutte B, Henfling M, Kolgen W, et al. Keratin 8/18 break-down and reorganization during apoptosis. Exp Cell Res 2004; 297(1):11-26.
14. Kadyrov M, Kaufmann P, Huppertz B. Expression of a cytokeratin 18 neo-epitope is a specific marker for trophoblast apoptosis in human placenta. Placenta 2001; 22(1): 44-8.
15. Valgimigli M, Merli E, Malagutti P, et al. Endothelial dysfunction in acute and chronic coronary syndromes: evidence for a pathogenetic role of oxidative stress. Arch Biochem Biophys 2003; 420(2):255-61.
16. Topol E J. Toward a new frontier in myocardial reperfusion therapy: emerging platelet preeminence. Circulation 1998; 97(2):211-8.
17. Rentrop K P. Thrombi in acute coronary syndromes: revisited and revised. Circulation 2000; 101(13):1619-26.
18. Mach F, Schonbeck U, Sukhova G K, et al. Functional CD40 ligand is expressed on human vascular endothelial cells, smooth muscle cells, and macrophages: implications for CD40-CD40 ligand signaling in atherosclerosis. Proc Natl Acad Sci USA 1997; 94(5):1931-6.
19. Aukrust P, Muller F, Ueland T, et al. Enhanced levels of soluble and membrane-bound CD40 ligand in patients with unstable angina. Possible reflection of T lymphocyte and platelet involvement in the pathogenesis of acute coronary syndromes. Circulation 1999; 100(6):614-20.
20. Ohashi Y, Kawashima S, Mori T, et al. Soluble CD40 ligand and interleukin-6 in the coronary circulation after acute myocardial infarction. Int J Cardiol 2005.
21. Mutin M, Canavy I, Blann A, Bory M, Sampol J, Dignat-George F. Direct evidence of endothelial injury in acute myocardial infarction and unstable angina by demonstration of circulating endothelial cells. Blood 1999; 93(9): 2951-8.
22. Valgimigli M, Agnoletti L, Curello S, et al. Serum from patients with acute coronary syndromes displays a proapoptotic effect on human endothelial cells: a possible link to pan-coronary syndromes. Circulation 2003; 107(2):264-70.
23. Braunwald E. Unstable angina. A classification. Circulation 1989; 80(2):410-4.
24. Rossi M L, Marziliano N, Merlini P A, et al. Different quantitative apoptotic traits in coronary atherosclerotic plaques from patients with stable angina pectoris and acute coronary syndromes. Circulation 2004; 110(13):1767-73.
25. Zal B, Kaski J C, Arno G, et al. Heat-shock protein 60-reactive CD4+CD28null T cells in patients with acute coronary syndromes. Circulation 2004; 109(10):1230-5.
26. Yaoita H, Ogawa K, Maehara K, Maruyama Y. Attenuation of ischemia/reperfusion injury in rats by a caspase inhibitor. Circulation 1998; 97(3):276-81.
27. Willseron J T. Sytemic and local inflammation in patients with unstable atherosclerotic plaques. Prog. Cardiovasc Dis 2002; 44(6):569-78.

The invention claimed is:

1. A method for diagnosing a cardiovascular disease involving thrombosis, or diagnosing stable and/or unstable angina pectoris in an individual comprising:
   determining an amount of caspase-cleaved cytokeratin-18 (CK-18) fragment in a sample from an individual;
   comparing the amount of caspase-cleaved CK-18 fragment in said sample to the amount of caspase-cleaved CK-18 fragment in a reference control of at least one individual not suffering from a cardiovascular disease involving thrombosis and/or a reference control of at least one individual suffering from stable angina pectoris or unstable angina pectoris; and
   diagnosing a cardiovascular disease involving thrombosis, or providing information to one who will diagnose cardiovascular disease involving thrombosis, if the amount of caspase-cleaved CK-18 fragment in the sample is increased in comparison to the amount of caspase-cleaved CK-18 fragment in the reference control from the at least one individual not suffering from a cardiovascular disease involving thrombosis, diagnosing stable angina pectoris, or providing information to one who will diagnose stable angina pectoris, if the amount of caspase-cleaved CK-18 fragment in the sample is decreased in comparison to the amount of caspase-cleaved CK-18 fragment in the reference control from the at least one individual suffering from unstable angina pectoris and/or if the amount of caspase-cleaved CK-18 fragment in the sample does not diverge with statistical significance from the amount of caspase-cleaved CK-18 fragment in the reference control from the at least one individual suffering from stable angina pectoris, and/or diagnosing unstable angina pectoris, or providing information to one who will diagnose unstable angina pectoris, if the amount of caspase-cleaved CK-18 fragment in the sample is increased in comparison to the amount of caspase-cleaved CK-18 fragment in the reference control from the at least one individual suffering from stable angina pectoris and/or if the amount of caspase-cleaved CK-18 fragment in the sample does not diverge with statistical significance from the amount of caspase-cleaved CK-18 fragment in the reference control from the at least one individual suffering from unstable angina pectoris.

2. The method of claim 1, wherein the cardiovascular disease involving thrombosis is atherosclerosis, coronary heart disease, an acute coronary symptom, stable angina pectoris, stroke, inflammation or autoimmune disease associated atherosclerosis, or restenosis.

3. The method of claim 1, wherein the cardiovascular disease involving thrombosis is unstable angina pectoris, acute myocardial infarction, or ischemic stroke.

4. The method of claim 1, further comprising determining an amount of caspase-1 (ICE) in the sample, comparing said amount of ICE in the sample to the amount of ICE present in the reference control, and diagnosing a cardiovascular disease involving thrombosis if there is an increased amount of ICE in the sample to the amount of ICE in the reference control.

5. The method of claim 1, further comprising determining an amount of caspase-1 (ICE) in the sample, comparing said amount of ICE in the sample to the amount of ICE present in the reference control, and diagnosing stable angina pectoris if the amount of ICE in the sample is decreased when compared to the amount of ICE in the reference control of at least one individual suffering from unstable angina pectoris.

6. The method of claim 1, wherein the amount of caspase-cleaved CK-18 fragment is immunologically determined.

7. The method of claim 6, wherein the amount of caspase-cleaved CK-18 fragment is determined by enzyme linked immunosorbent assay, radioimmunoassay, or Western blot analysis.

8. The method of claim 1, wherein the sample is a blood sample.

9. The method of claim 8, wherein the sample is a plasma or serum sample.

10. The method of claim 8, wherein the sample is obtained from the femoral artery.

11. The method of claim 1, further comprising determining an amount of interleukin-1β precursor (IL-1β precursor) in said sample; and comparing the amount of IL-1β precursor in said sample to the amount of IL-1β precursor present in a reference control of at least one individual not suffering from a cardiovascular disease involving thrombosis.

12. The method of claim 11, further comprising diagnosing a cardiovascular disease involving thrombosis if the amount of caspase-cleaved CK-18 fragment in the sample is increased in comparison to the amount of caspase-cleaved CK-18 fragment in the reference control and/or the amount of IL-1β precursor in the sample is decreased in comparison to the amount of IL-1β precursor in the reference control.

13. The method of claim 12, wherein the cardiovascular disease involving thrombosis is atherosclerosis, coronary heart disease, an acute coronary symptom, stable angina pectoris, stroke, inflammation or autoimmune disease associated arteriosclerosis, or restenosis.

14. The method of claim 12, wherein the cardiovascular disease involving thrombosis is unstable angina pectoris, acute myocardial infarction, or ischemic stroke.

15. The method of claim 11, further comprising diagnosing stable angina pectoris if the amount of caspase-cleaved CK-18 fragment in the sample is decreased and/or the amount of IL-1β precursor in the sample is increased in comparison to amount of caspase-cleaved CK-18 fragment and/or IL-1β precursor in the reference control of at least one individual suffering from unstable angina pectoris.

16. The method of claim 11, wherein the amount of interleukin-1β precursor (IL-1β precursor) is immunologically determined.

17. The method of claim 16, wherein the amount of IL-1β precursor is determined by enzyme linked immunosorbent assay, radioimmunoassay, or Western blot analysis.

* * * * *

UNITED STATES PATENT AND TRADEMARK OFFICE
CERTIFICATE OF CORRECTION

PATENT NO. : 8,129,135 B2  
APPLICATION NO. : 12/298209  
DATED : March 6, 2012  
INVENTOR(S) : Jan Hendrik Ankersmit It is certified that error appears in the above-identified patent and that said Letters Patent is hereby corrected as shown below:

In claim 13, column 26, line 12, delete "arteriosclerosis" and insert --artheriosclerosis-- therefor.

Signed and Sealed this
Seventeenth Day of April, 2012

David J. Kappos
*Director of the United States Patent and Trademark Office*